(12) United States Patent
Burbelo et al.

(10) Patent No.: US 8,951,723 B2
(45) Date of Patent: Feb. 10, 2015

(54) SEROLOGICAL SCREENING FOR HHV-8 INFECTION USING ANTIGEN MIXTURES

(75) Inventors: Peter D. Burbelo, Washington, DC (US); Joseph Kovacs, Bethesda, MD (US); Michael J. Iadarola, Chevy Chase, MD (US)

(73) Assignee: The United States of America as Represented by the Secretary, Department of Health and Human Services, Washington, DC (US)

( * ) Notice: Subject to any disclaimer, the term of this patent is extended or adjusted under 35 U.S.C. 154(b) by 224 days.

(21) Appl. No.: 13/201,317

(22) PCT Filed: Feb. 12, 2010

(86) PCT No.: PCT/US2010/024104
§ 371 (c)(1),
(2), (4) Date: Aug. 12, 2011

(87) PCT Pub. No.: WO2010/093924
PCT Pub. Date: Aug. 19, 2010

(65) Prior Publication Data
US 2011/0294147 A1 Dec. 1, 2011

Related U.S. Application Data

(60) Provisional application No. 61/152,058, filed on Feb. 12, 2009.

(51) Int. Cl.
*C12Q 1/70* (2006.01)
*G01N 33/569* (2006.01)

(52) U.S. Cl.
CPC ...... *G01N 33/56994* (2013.01); *G01N 2333/03* (2013.01); *C12N 2710/16422* (2013.01)
USPC ................................................. 435/5; 435/7.1

(58) Field of Classification Search
CPC .................... G01N 2333/03; G01N 33/56994; C12N 2710/16422
See application file for complete search history.

(56) References Cited

U.S. PATENT DOCUMENTS 6,348,586 B1 * 2/2002 Chang et al. ............... 536/23.72
6,669,939 B1 * 12/2003 Schatz et al. ............... 424/185.1

FOREIGN PATENT DOCUMENTS

| FR | 2782519 A1 | 2/2000 |
|---|---|---|
| WO | 9724057 A2 | 7/1997 |
| WO | 9815289 A1 | 4/1998 |
| WO | 9961909 A2 | 12/1999 |
| WO | 2009020628 A1 | 2/2009 |

OTHER PUBLICATIONS

Van Dross et al (Journal of the National Cancer Institute 97:656-666, 2005).*
Laney et al., "Use of a Multiantigen Detection Algorithm for Diagnosis of Kaposi's Sarcoma-Associated Herpesvirus Infection", Journal of Clinical Microbiology, vol. 44, No. 10, pp. 3734-3741 (2006).
Jenkins et al., "Human Herpesvirus 8 Seroprevalence among Prostate Cancer Patients and Control Subjects", Journal of Infectious Diseases, vol. 196, No. 2, pp. 208-211 (2007).
Cesarman et al., "Kaposi's Sarcoma-Associated Heresvirus Contains G Protein-Coupled Receptor and Cyclin D Homologs Which are Expressed in Kaposi's Sarcoma and Malignant Lymphoma", Journal of Virology, The American Society for Microbiology, vol. 70, No. 11, pp. 8218-8223 (1996).
Neipel et al., "Cell-Homologous Genes in the Kaposi's Sarcoma-Associated Rhadinovirus Human Herpesvirus 8: Determinants of Its Pathogenicity", Journal of Virology, vol. 71, No. 6, pp. 4187-4192 (1997).
Raab et al., "The Immunogenic Glycoprotein gp35-37 of Human Herpesvirus 8 Is Encoded by Open Reading Frearn K8.1", Journal of Virology, vol. 72, No. 8, pp. 6725-6731 (1998).
Glenn et al., "Identification of a Spliced Gene from Kaposi's Sarcoma-Associated Herpesvirus Encoding a Protein with Similarities to Latent Membrane Proteins 1 and 2A of Epstein-Barr Virus", Journal of Virology, vol. 73, No. 8, pp. 6953-6963 (1999).
Chandran et al., "Human Herpe virus-8 ORF K8.1 Gene Encodes Immunogenic Glycoproteins Generated by Spliced Transcripts", Virology, vol. 249, No. 1, pp. 140-149 (1998).
Burbelo et al., "Four-Antigen Mixture Containing V-Cyclin for Serological Screening of Human Herpesvirus 8 Infection", Clinical and Vaccine Immunology, vol. 16, No. 5, pp. 627-627 (2009).
Burbelo et al., "Rapid antibody quantification and generation of whole proteome antibody response profiles using LIPS (luciferase immunoprecipitation systems)", Biochemical and Biophysical Research Communications, vol. 352, No. 4, pp. 889-895 (2007).

* cited by examiner

*Primary Examiner* — Mary E Mosher
(74) *Attorney, Agent, or Firm* — Edwards Wildman Palmer

(57) ABSTRACT

The invention provides compositions, methods, and kits for the diagnosis or detection of active, latent, or prior infection with human herpesvirus 8 in a subject sample.

17 Claims, 6 Drawing Sheets

```
              FLAG epitope                        Ruc
atcagccgccacc atggactacaaggacgacgatgacaagggatctacttcgaaa..  (13)
              M  D  Y  K  D  D  D  D  K  G  S  T  S  K...   (14)

BamHI EcoRI    HindIII XhoI      XbaI
aaaaatgaacaaggatccgaattcaaaaagcttctcgagagtacttctagagcg       (15)
K  N  E  Q  G  S  E  F  K  K  L  L  E  S  T  S  R  A         (16)
```

US 8,951,723 B2

SEROLOGICAL SCREENING FOR HHV-8 INFECTION USING ANTIGEN MIXTURES

CROSS-REFERENCE TO RELATED APPLICATIONS

This application is a 35 U.S.C. §371 U.S. national entry of International Application PCT/US 2010/024104(WO 2010/093924) having an International filing date of Feb. 12, 2010, which claims priority to Provisional Patent Application Ser. No. 61/152,058 filed on Feb. 12, 2009, both of which are incorporated herein by reference in their entirety.

GOVERNMENT SUPPORT

This work was supported by the Intramural Research Program of the National Institutes of Health, the National Institute of Dental and Craniofacial Research, the NIH Clinical Center, and the National Cancer Institute and, in part, by a Bench to Bedside award from the NIH Clinical Center. The Government has certain rights to this invention.

BACKGROUND

Kaposi sarcoma (KS) is an opportunistic disease in HIV patients and the most common cancer associated with AIDS worldwide. Identified a decade ago as the causative agent of KS, the human herpes virus 8 (HHV-8), also known as Kaposi's sarcoma-associated herpes virus (KSHV), has a 125 kb genome encoding approximately 90 gene products. Many of these gene products allow the virus to evade the human immune system. KS primarily affects AIDS patients, but it can also occur in non-HIV-infected individuals and presents as classical, endemic or post-transplant forms. HHV-8 also causes two other rare B-cell cancers, primary effusion lymphoma (PEL) and multicentric Castleman disease (MCD), which are primarily found in HIV-infected or other immunosupressed patients.

Currently, there is a need for sensitive and specific testing to identify HHV-8 infected individuals, especially among potential blood and/or organ donors. Low viral loads in blood limit the sensitivity and thus usefulness of PCR-based approaches. Alternatively, a variety of serological tests have been tried to detect antibodies to HHV-8 proteins and diagnose infection using various target antigens, all with limited success.

SUMMARY OF THE INVENTION

The invention provides methods of detecting active, latent, or prior HHV8 infection of a subject sample, by contacting the subject sample with at least an antigenic fragment of an HHV-8 v-cyclin polypeptide and detecting specific binding of an antibody in the sample that specifically binds to the antigenic fragment of the HHV-8 v-cyclin. Specific binding of an antibody to the antigenic fragment of the HHV-8 v-cyclin indicates an HHV-8 infection of the subject. In certain embodiments, the antigenic fragment of v-cyclin includes the sequence of at least amino acids 2 to 257 of SEQ ID NO: 3.

The invention further includes assays for detecting HHV8 infection using multiple antigens from HHV8. In certain embodiments, the methods include contacting the subject sample with at least one additional antigenic fragment, for example one, two, three, four, five, six, seven, eight, nine, or ten additional antigenic fragments. The additional antigenic fragment is one or more of an antigenic fragment of an HHV-8 K8.1 polypeptide (SEQ ID NO: 1), an antigenic fragment of an HHV-8 ORF65 polypeptide (SEQ ID NO: 2), and an antigenic fragment of an HHV-8 LANA polypeptide (SEQ ID NO: 4). In certain embodiments, the at least an antigenic fragment of HHV-8 K8.1 polypeptide (SEQ ID NO: 1) includes one or more sequences from the group of a polypeptides having the sequence of amino acids 25-228, amino acids 143-228, amino acids 2-228, amino acids 1-141, and amino acids 25-141 of SEQ ID NO: 1. In certain embodiments, the at least an antigenic fragment of ORF65 polypeptide (SEQ ID NO: 2) is the polypeptide sequence of amino acids 2-170 of SEQ ID NO: 2. In certain embodiments, the at least an antigenic fragment of HHV-8 LANA polypeptide (SEQ ID NO: 4) includes one or more sequences from the group polypeptides of amino acids 274-925, amino acids 6-286, amino acids 6-925, amino acids 58-286, amino acids 58-925, amino acids 286-925, amino acids 286-863, amino acids 6-863, and amino acids 58-863 of SEQ ID NO: 4.

In certain embodiments, two or more (e.g., 2, 3, 4, 5, 6, 7, 8, etc.) of the antigens are present in a single reaction mixture. In certain embodiments, the antigens are present in a single reaction mixture. In certain embodiments, binding to the antigens are tested essentially simultaneously, either in a single reaction or parallel reactions, such that the results of all of the tests are considered together. In certain embodiments, binding to the antigens are tested sequentially, such that the data from one binding assay is considered prior to the next test. In certain embodiments, more than two antigenic sequences based on a single full length sequence (SEQ ID NOs: 1-4) are tested. In certain embodiments, each of the antigenic fragments includes a sequence from a different amino acid sequence provided in SEQ ID NO: 1-4.

In certain embodiments, the antigenic fragments used in the detection method include HHV-8 LANA-Δ2 (SEQ ID NO: 8), antigenic fragment of an HHV-8 K8.1-Δ4 (SEQ ID NO: 5), antigenic fragment of an HHV-8 v-cyclin (SEQ ID NO: 7), and antigenic fragment of an HHV-8 ORF65 (SEQ ID NO: 6).

The methods of the invention can further include identifying a subject having or suspected of having an HHV8 infection. The method also provides for stratification of subjects based on the antibodies detected in the subject sample. For example, the invention provides methods for comparing an amount of antibody bound to an antigenic fragment of v-cyclin or an antigenic fragment of LANA to an amount of antibody bound to an amount of antibody bound to an antigenic fragment of ORF65, wherein a greater amount of antibody binding to an antigenic fragment of v-cyclin or an antigenic fragment of LANA relative to an antigenic fragment of ORF65 indicates a lytic HHV-8 infection; and a greater amount of antibody binding to an antigenic fragment of ORF65 relative to an antigenic fragment of v-cyclin or an antigenic fragment of LANA indicates a latent infection in the subject.

The methods of the invention include methods for testing an individual, or for screening samples for transfusion or donation into a recipient. For example, the methods can be used to screen the blood supply after collection from donors to insure the safety of the blood supply. The methods can be used to test tissues and organs from donors, including cadaver donors, to insure that the organ or tissue for transplantation is not infected with HHV8.

The methods of the invention include any immunoassay format including, but not limited to LIPS assay, ELISA, immunoprecipitation assay, dot blot, slot blot, western blot, immunofluorescence assay, and particle based flow cytometric detection. In a preferred embodiment, the subject sample is contacted with the antigen in solution. After formation of the antigen-antibody complex in solution, the complex is captured and detected.

In certain embodiments of the invention, the subject has not been diagnosed with Kaposi's sarcoma. In certain embodiments of the invention, the subject has been diagnosed with Kaposi's sarcoma.

The methods of the invention provide highly specific and highly sensitive methods for detection of HHV8 infection. For example, the methods of detecting can provide a sensitivity of at least 95% and a specificity of at least 95%. In certain embodiments, the methods of detecting provides a sensitivity of at least 96%, 97%, 98%, or 99%. In certain embodiments, the methods of detecting provide a specificity of at least 96%, 97%, 98%, or 99%.

The invention provides kits for practicing any of the methods of the invention.

The invention provides compositions including any combination of antigens, either as the antigens alone, or in combination with reporter polypeptides, epitope tags, spacers, etc for use in the methods of the invention. The invention further provides expression constructs, alone or in combination, for expression of any of the antigens of the invention, either alone or as fusion constructs with reporter polypeptides, epitope tags, spacers, etc. Nucleic acid sequences encoding the polypeptides in SEQ ID NOs: 1-4 (K8.1, ORF65, v-cyclin, and LANA) are provided in SEQ ID NOs: 9-12, respectively.

The invention provides compositions including at least one antigenic fragment of one of the following polypeptides:

a) an isolated polypeptide sequence of amino acids 25-228, amino acids 143-228, amino acids 2-228, amino acids 1-141, and amino acids 25-141 of SEQ ID NO: 1;

b) an isolated polypeptide sequence of amino acids 2-170 of SEQ ID NO: 2;

c) an isolated polypeptide sequence of amino acids 2-257 of SEQ ID NO: 3; and d) an isolated polypeptide sequence of amino acids 274-925, amino acids 6-286, amino acids 6-925, amino acids 58-286, amino acids 58-925, amino acids 286-925, amino acids 286-863, amino acids 6-863, and amino acids 58-863 of SEQ ID NO: 4.

The invention provides compositions that are combinations of at least antigenic fragments of the polypeptides provided in a, b, c, and d. For example, the invention provides for combinations of polypeptides including pairs of polypeptides such as one from each of a and b, a and c, a and d, b and c, b and d, and c and d. The invention provides for groups of three peptides for example combinations of at least one peptide from a, b, and c; a, b, and d; a, c, and d; and b, c, and d. The invention provides for combinations of any one of the polypeptides listed in each of a, b, c, and d.

In certain embodiments, the compositions provided include antigenic polypeptides comprise or consist essentially of an antigenic fragment selected from the group consisting of the polypeptide sequence of amino acids 25-228 of SEQ ID NO: 1, amino acids 2-170 of SEQ ID NO: 2, amino acids 2-257 of SEQ ID NO: 3, and amino acids 274-925 of SEQ ID NO: 4, that is the same as SEQ ID NO: 5, 6, 7, and 8.

In certain embodiments, the antigenic polypeptides are covalently linked to a reporter polypeptide, for example by a peptide bond. However, any other covalent chemical linkage can be used that does not disrupt the function of the antigenic fragment and the reporter polypeptide. A number of reporter peptides are known in the art including, but not limited to, luciferase, beta-galactosidase, and alkaline phosphatase. Appropriate substrates for each of the reporter polypeptides are known in the art and commercially available.

The invention provides nucleic acids for encoding any of the polypeptide sequences of the instant invention. The nucleic acids are preferably in an expression vector, such as a plasmid vector, where the encoding sequence is operably linked to appropriate transcription and translation control sequences. Such expression vectors and control sequences are well known to those of skill in the art. The invention further includes mixtures of nucleic acids for encoding two or more of the polypeptides of the invention including mixtures of 2, 3, 4, 5, 6, 7, 8, 9, or 10 of the polypeptides of the invention. The invention also includes single polypeptides for encoding multiple polypeptides of the invention.

The invention further provides other embodiments that are provided infra.

Shown are results from 34 uninfected controls, 35 KS, 14 MCD+/KS+, 6 MCD+/KS−, and 5 PEL patients. Each symbol represents a serum sample from an individual patient. The geometric mean antibody titer and 95% CI for (A) anti-K8.1 lytic antibodies, (B) anti-v-cyclin latent antibody and (C) anti-LANA antibody titers in LU are plotted on the Y-axis using a $\log^{10}$ scale. The dashed line represents the cut-off level for determining seropositivity and is derived from the mean plus 5 SD of the antibody titer of the 34 uninfected controls. All the uninfected controls were negative for all KHSV antibodies and were below the established cut-off. (D) Sum of anti-v-cyclin and anti-LANA antibodies. The solid line represents the optimum cut-off (70,000 LU) for discriminating the KS from the MCD+/KS− patients, while a higher cut-off (165,000 LU) shown by the dotted line optimally separated the KS from the MCD+/KS+ patients. All P values were calculated using the Mann Whitney U test.

Figure 6:
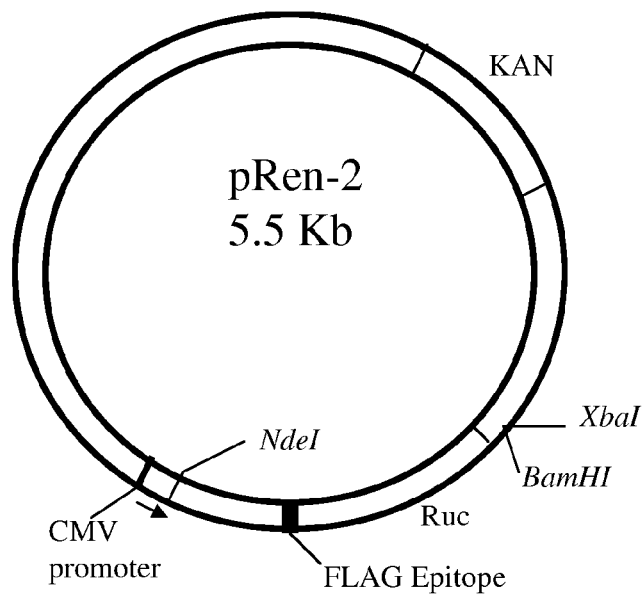

FIG. 6. Schematic of the pREN2 mammalian expression vector. Features indicated are CMV (cytomegalovirus) promoter, the N-terminal FLAG epitope and Ruc. Sequences for Ruc are in bold. cDNAs for tumor antigens were cloned downstream of Ruc between the BamHI-XhoI sites. Sequences of the FLAG-epitope operably linked to luciferase (SEQ ID NO: 13 and 14) and the multiple cloning site (SEQ ID NO: 15 and 16) are provided.

Table 1 shows performance of the top 10 antigens in the LIPS assay.

Table 2 shows the antigens tested using the LIPS assay and corresponding SEQ ID NOs. GenBank numbers refer to Version 1 of each of the sequences available as of Feb. 12, 2009.

DEFINITIONS

"Antigenic fragment" and the like are understood as at least that portion of a peptide capable of inducing an immune response in a subject, or being able to be bound by an autoantibody present in a subject having or suspected of having a viral infection, particularly an HHV-8 infection, particularly when the antigen includes a partial sequence of consecutive amino acids of at least one of the following proteins: K8.1, v-cyclin (ORF72), ORF65 and a LANA (ORF73). Typically, antigenic fragments are at least 7 amino acids in length. Moreover, common epitopes for viral antigens have been mapped and can be used as antigenic fragments in the compositions and methods provided herein. Antigenic fragments can include deletions of the amino acid sequence from the N-terminus or the C-terminus, or both. For example, an antigenic fragment can have an N- and/or a C-terminal deletion of about 1, 2, 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 200, 300, 400, 500, 600, or more amino acids. Antigenic fragments can also include one or more internal deletions of the same exemplary lengths. Antigenic fragments can also include one or more point mutations, particularly conservative point mutations. At least an antigenic fragment of protein can include the full length, wild-type sequence of the antigen. An antigenic fragment can include more than one potential antibody binding site.

As used herein, "binding" is understood as having at least a $10^2$ or more, $10^3$ or more, preferably $10^4$ or more, preferably $10^5$ or more, preferably $10^6$ or more preference for binding to a specific binding partner as compared to a non-specific binding partner (e.g., binding an antigen to a sample known to contain the cognate antibody).

As used herein, "changed as compared to a control" sample or subject is understood as having a level of the analyte or diagnostic or therapeutic indicator to be detected at a level that is statistically different than a sample from a normal, untreated, or control sample. Control samples include, for example, cells in culture, one or more laboratory test animals, or one or more human subjects. Methods to select and test control samples are within the ability of those in the art. An analyte can be a naturally occurring substance that is characteristically expressed or produced by the cell or organism (e.g., an antibody, a protein) or a substance produced by a reporter construct (e.g, β-galactosidase or luciferase). Depending on the method used for detection the amount and measurement of the change can vary. Changed as compared to a control reference sample can also include a change in one or more signs or symptoms associated with or diagnostic of HHV-8 infection. Determination of statistical significance is within the ability of those skilled in the art, e.g., the number of standard deviations from the mean that constitute a positive result.

"Consisting essentially of" is understood to have the meaning assigned is US patents as limiting the scope of a claim to the specified materials or steps "and those that do not materially affect the basic and novel characteristic(s)" of the claimed invention. As used herein in reference to antigenic polypeptides, "consisting essentially of" is understood as an antigenic polypeptide sequence including the claimed sequence, and optionally further containing other elements or optionally having shorter amino acid sequences than presented that do not materially affect the basic and novel characteristics of the antigenic polypeptide. That is, other elements or deletion of sequences that neither substantially inhibit or enhance binding of the peptide to cognate antibodies in a subject sample, or decrease the specificity of the binding of the antigen to a subject sample. In certain embodiments, antigenic fragments of longer polypeptides can be expressed to include an initiator methionine, a signal sequence for translocation of the protein, or may include sequences at the N- or C-terminus after cleavage with a protease not present in the native sequence. For example, an antigenic polypeptide sequence that consists essentially of a defined antigen sequence includes the defined sequence an optionally other elements such that the antigenic polypeptide consisting essentially of the defined antigen sequence can compete with the antigenic polypeptide for binding to a positive serum sample at a molar ratio of 10:1 to 1:10, or 5:1 to 1:5, preferably at a molar ratio of 2:1 to 1:2, and the binding to a non-specific antigen. As used herein, a polypeptide consisting essentially of an antigenic fragment can be linked covalently (e.g., by a peptide bond or other linkage) to a second polypeptide, for example a reporter polypeptide, or an epitope tag (e.g., a FLAG tag).

"Contiguous" is understood as touching or connected to through an unbroken sequence.

As used herein, "detecting", "detection" and the like are understood that an assay performed for identification of a specific analyte in a sample, e.g., an antibody in a sample. The amount of analyte or activity detected in the sample can be none or below the level of detection of the assay or method.

By "diagnosing" and the like as used herein refers to a clinical or other assessment of the condition of a subject based on observation, testing, or circumstances for identifying a subject having a disease, disorder, or condition based on the presence of at least one indicator, such as a sign or symptom of the disease, disorder, or condition. Typically, diagnosing using the method of the invention includes the observation of the subject for multiple indicators of the disease, disorder, or condition in conjunction with the methods provided herein. A diagnostic methods provide an indicator that a disease is or is not present. A single diagnostic test typically does not provide a definitive conclusion regarding the disease state of the subject being tested.

As used herein, the terms "identity" or "percent identity", refers to the subunit sequence similarity between two polymeric molecules, e.g., two polynucleotides or two polypeptides. When a subunit position in both of the two molecules is occupied by the same monomeric subunit, e.g., if a position in each of two peptides is occupied by serine, then they are identical at that position. The identity between two sequences is a direct function of the number of matching or identical positions, e.g., if half (e.g., 5 positions in a polymer 10 subunits in length), of the positions in two peptide or compound sequences are identical, then the two sequences are 50% identical; if 90% of the positions, e.g., 9 of 10 are matched, the two sequences share 90% sequence identity. The identity between two sequences is a direct function of the number of matching or identical positions. Thus, if a portion of the reference sequence is deleted in a particular peptide, that deleted section is not counted for purposes of calculating sequence identity. Identity is often measured using sequence analysis software e.g., BLASTN or BLASTP (available on the internet at (ncbi.nih.gov/BLAST). The default parameters for comparing two sequences (e.g., "Blast"-ing two sequences against each other), by BLASTN (for nucleotide sequences) are reward for match=1, penalty for mismatch=-2, open gap=5, extension gap=2. When using BLASTP for protein sequences, the default parameters are reward for match=0, penalty for mismatch=0, open gap=11, and extension gap=1. Additional, computer programs for determining identity are known in the art.

As used herein, "isolated" or "purified" when used in reference to a polypeptide or nucleic acid means that a naturally polypeptide or nucleic acid has been removed from its normal physiological environment (e.g., protein isolated from plasma or tissue, optionally bound to another protein) or is synthesized in a non-natural environment (e.g., artificially synthesized in an in vitro transcription or translation system or using chemical synthesis). Thus, an "isolated" or "purified" polypeptide can be in a cell-free solution or placed in a different cellular environment (e.g., expressed in a heterologous cell type). The term "purified" does not imply that the polypeptide is the only polypeptide present, but that it is essentially free (about 90-95%, up to 99-100% pure) of cellular or organismal material naturally associated with it, and thus is distinguished from naturally occurring polypeptide. Similarly, an isolated nucleic acid is removed from its normal physiological environment. "Isolated" when used in reference to a cell means the cell is in culture (i.e., not in an animal), either cell culture or organ culture, of a primary cell or cell line. Cells can be isolated from a normal animal, a transgenic animal, an animal having spontaneously occurring genetic changes, and/or an animal having a genetic and/or induced disease or condition. An isolated virus or viral vector is a virus that is removed from the cells, typically in culture, in which the virus was produced.

As used herein, "kits" are understood to contain at least one non-standard laboratory reagent for use in the methods of the invention in appropriate packaging, optionally containing instructions for use. The kit can further include any other components required to practice the method of the invention, as dry powders, concentrated solutions, or ready to use solutions. In some embodiments, the kit comprises one or more containers that contain reagents for use in the methods of the invention; such containers can be boxes, ampules, bottles, vials, tubes, bags, pouches, blister-packs, or other suitable container forms known in the art. Such containers can be made of plastic, glass, laminated paper, metal foil, or other materials suitable for holding reagents.

As used herein, a "nucleic acid encoding a polypeptide" is understood as any possible nucleic acid that upon (transcription and) translation would result in a polypeptide of the desired sequence. The degeneracy of the nucleic acid code is well understood. Further, it is well known that various organisms have preferred codon usage, etc. Determination of a nucleic acid sequence to encode any polypeptide is well within the ability of those of skill in the art.

"Obtaining" is understood herein as manufacturing, purchasing, or otherwise coming into possession of.

As used herein, "operably linked" is understood as joined, preferably by a covalent linkage, e.g., joining an amino-terminus of one peptide, e.g., expressing an enzyme, to a carboxy terminus of another peptide, e.g., expressing a signal sequence to target the protein to a specific cellular compartment; joining a promoter sequence with a protein coding sequence, in a manner that the two or more components that are operably linked either retain their original activity, or gain an activity upon joining such that the activity of the operably linked portions can be assayed and have detectable activity, e.g., enzymatic activity, protein expression activity.

As used herein, "plurality" is understood to mean more than one. For example, a plurality refers to at least two, three, four, five, or more.

A "polypeptide" or "peptide" as used herein is understood as two or more independently selected natural or non-natural amino acids joined by a covalent bond (e.g., a peptide bond). A peptide can include 2, 3, 4, 5, 6, 7, 8, 9, 10, 11, 12, 13, 14, 15, 16, 17, 18, 19, 20, or more natural or non-natural amino acids joined by peptide bonds. Polypeptides as described herein include full length proteins (e.g., fully processed proteins) as well as shorter amino acids sequences (e.g., fragments of naturally occurring proteins or synthetic polypeptide fragments).

A "sample" as used herein refers to a biological material that is isolated from its environment (e.g., blood or tissue from an animal, cells, or conditioned media from tissue culture) and is suspected of containing, or known to contain an analyte, such as an autoantibody. A sample can also be a partially purified fraction of a tissue or bodily fluid (e.g., serum or plasma). A reference sample can be a "normal" sample, from a donor not having the disease or condition fluid, or from a normal tissue in a subject having the disease or condition. A reference sample can also be from an untreated donor or cell culture not treated with an active agent (e.g., no treatment or administration of vehicle only). A reference sample can also be taken at a "zero time point" prior to contacting the cell or subject with the agent or therapeutic intervention to be tested or at the start of a prospective study.

"Sensitivity and specificity" are statistical measures of the performance of a binary classification test. The sensitivity (also called recall rate in some fields) measures the proportion of actual positives which are correctly identified as such (e.g. the percentage of sick people who are identified as having the condition); and the specificity measures the proportion of negatives which are correctly identified (e.g. the percentage of well people who are identified as not having the condition). They are closely related to the concepts of type I and type II errors. A theoretical, optimal prediction can achieve 100% sensitivity (i.e. predict all people from the sick group as sick) and 100% specificity (i.e. not predict anyone from the healthy group as sick).

The concepts are expressed mathematically as follows:

sensitivity=# true positives/# true positives+# false negatives specificity=# true negatives/# true negatives+# false positives.

A "subject" as used herein refers to an organism. In certain embodiments, the organism is an animal. In certain embodiments, the subject is a living organism. In certain embodiments, the subject is a cadaver organism. In certain preferred embodiments, the subject is a mammal. In certain embodiments, the subject is a domesticated mammal or a primate including a non-human primate. In certain preferred embodiments, the subject is a mammal that is capable of being infected by HHV-8. Examples of subjects include humans, monkeys, dogs, cats, mice, rats, cows, horses, goats, and sheep. A human subject may also be referred to as a patient.

A "subject sample" can be a sample obtained from any subject, typically a blood or serum sample, however the method contemplates the use of any body fluid or tissue from a subject. The sample may be obtained, for example, for diagnosis of a specific individual for the presence or absence of HHV-8 infection. In certain embodiments, a subject sample can be a sample for screening of a subject tissue (solubilized or treated to release antibodies) or body fluid (e.g., blood, serum, plasma) prior to transplant or transfusion into a recipient.

A subject "suffering from or suspected of suffering from" a specific disease, condition, or syndrome has a sufficient number of risk factors or presents with a sufficient number or combination of signs or symptoms of the disease, condition, or syndrome such that a competent individual would diagnose or suspect that the subject was suffering from the disease, condition, or syndrome. Methods for identification of subjects suffering from or suspected of suffering from conditions such as HHV8 infection is within the ability of those in the art. Subjects suffering from, and suspected of suffering from, a specific disease, condition, or syndrome are not necessarily two distinct groups.

As used herein, "susceptible to" or "prone to" or "predisposed to" a specific disease or condition and the like refers to an individual who based on genetic, environmental, health, and/or other risk factors is more likely to develop a disease or condition than the general population. An increase in likelihood of developing a disease may be an increase of about 10%, 20%, 50%, 100%, 150%, 200%, or more.

As used herein, a "reporter protein" or a "reporter polypeptide" is understood as a polypeptide that can be readily detected, preferably quantitatively detected, either directly or indirectly. A reporter polypeptide typically has an enzymatic activity, luciferase activity, alkaline phosphatase activity, beta-galactosidase activity, acetyl transferase activity, etc. wherein catalysis of a reaction with the substrate by the enzyme results in the production of a product, e.g., light, a product that can be detected at a specific wavelength of light, radioactivity, such that the amount of the reporter peptide can be determined in the sample, either as a relative amount, or as an absolute amount by comparison to control samples. The sequence of Renilla luciferase is provided, for example, in SEQ ID NO: 11.

Ranges provided herein are understood to be shorthand for all of the values within the range. This includes all individual sequences when a range of SEQ ID NOs: is provided. For example, a range of 1 to 50 is understood to include any number, combination of numbers, or sub-range from the group consisting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Unless specifically stated or obvious from context, as used herein, the term "or" is understood to be inclusive.

Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein can be modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

DETAILED DESCRIPTION OF THE INVENTION

Kaposi sarcoma-associated herpes virus (KSHV), also called human herpesvirus-8 (HHV-8), is the causative agent of all forms of Kaposi sarcoma (KS). In KS, most proliferating tumor spindle cells are infected with KSHV and express KSHV proteins. KSHV has a 170.5 kb genome encoding approximately 90 gene products and contains a number of pirated genes involved in cell proliferation, angiogenesis, and evasion of the immune system. KSHV is also the causative agent of two rare B-cell lymphoproliferative disorders, primary effusion lymphoma (PEL) and multicentric Castleman's disease (MCD), that occur primarily in patients infected with human immunodeficiency virus (HIV). PEL is characterized by its tendency to develop in body cavities such as pleural or peritoneal spaces. MCD is characterized clinically by fevers, wasting, hypoalbuminemia, and cytopenias that result from overproduction of viral-encoded and human-encoded cytokines, especially interleukin-6 (IL-6).

Like other herpesviruses, KSHV has two phases of gene expression, latent and lytic. In KS, a majority of KSHV-infected spindle cells express only latent genes, while a small percentage express lytic genes. By contrast, a substantial percentage of MCD cells express lytic KSHV genes, including a virally-encoded IL-6. The majority of PEL cells express KSHV latent genes, but in addition can show limited expression of certain lytic genes. Given the differential expression of KSHV lytic and latent proteins in KS, PEL, and MCD, we demonstrate herein that different antibody profiles to KSHV antigens detected by LIPS might distinguish these diseases.

Provided herein are four antigens for use in an immunoassay for the detection of infection with HHV8. The invention provides for the use of any antigenic fragment that efficiently competes for binding, at a ratio of 10:1 to 1:10, or 5:1 to 1:5, preferably at a ratio of 2:1 to 1:2, with at least one of K8.1-Δ4, ORF65 (full length), v-cyclin (full length), of LANA-Δ2 to a sample positive for HHV8. In an embodiment the immunoassay provides for the use of 1, 2, 3, or 4 of the antigens. In an embodiment, the immunoassay provides for the use of at least one of the full length v-cyclin protein without the initiator methionine; the full length ORF65 protein without the initiator methionine; a K8.1 antigen having the sequence of at least one of K8.1-Δ1, K8.1-Δ2, K8.1-Δ4, or K8.1-full length without the initiator methione; and a LANA antigen having the sequence of at least one of LANA-Δ1, LANA-Δ2, LANA-Δ3, LANA-Δ4, LANA-Δ5, or LANA-Δ6. In an embodiment, the immunoassay provides for the use of at least two of the full length v-cyclin protein without the initiator methionine; the full length ORF65 protein without the initiator methionine; a K8.1 antigen; and a LANA antigen. In an embodiment, the immunoassay provides for the use of at least three of the full length v-cyclin protein without the initiator methionine; the full length ORF65 protein without the initiator methionine; a K8.1 antigen; and a LANA antigen. In an embodiment, the immunoassay provides for the use of at least four of the full length v-cyclin protein without the initiator methionine; the full length ORF65 protein without the initiator methionine; a K8.1 antigen; and a LANA antigen. In an embodiment, the immunoassay provides for the use of . In an embodiment, the immunoassay provides for the use of at least two of the full length v-cyclin protein without the initiator methionine; the full length ORF65 protein without the initiator methionine; a K8.1 antigen K8.1-Δ4; and a LANA antigen LANA-Δ2.

We have developed a highly sensitive immunoprecipitation technology called Luciferase Immunoprecipitation System (LIPS) that utilizes mammalian cell-produced, recombinant fusion protein antigens for efficiently evaluating antibody responses (see US Patent Publication 2007/0259336 and Burbelo et al. 2005. *BMC Biotechnol.* 5:22, both of which are incorporated herein by reference). In a limited number of side-by-side comparisons, LIPS showed improved diagnostic performance compared to existing immunoassays for detecting antibodies to infectious agents and provided new tools to monitor drug treatment and sub-stratify disease states. In addition, LIPS is highly useful for profiling autoimmunity and in one study showed several advantages over a highly sensitive radioactive in vitro transcription/translation assay for detecting anti-IA2 autoantibodies associated with type I diabetes. In the present study, LIPS was evaluated for its diagnostic performance in detecting antibodies to HHV-8.

We demonstrate herein that Luciferase Immunoprecipitation Systems (LIPS) is a highly sensitive, specific and high-throughput method for diagnosis of HHV-8 infection. As part of this invention, we screened 13 potential HHV-8 antigens and discovered anti-v-cyclin antibodies as a new serological marker occurring in approximately 75% of KS (HHV-8-infected) sera. From our studies, we found that antibody profiling of 4 antigens (K8.1, v-cyclin, ORF65 and various LANA fragments) provided highly quantitative information for diagnosis. Analysis of a validation set using the combined results of these 4 separate antigen tests or using a 4 antigen mixture showed 100% sensitivity and 100% specificity and LIPS performed better then ELISA (94% sensitivity). The use of mixture containing all 4 HHV-8 antigens is a sensitive and efficient high-throughput method for serological screening of HHV-8 infection and is highly convenient because it simplifies data collection and analysis. The invention provides antigen mixtures including any combination of two, three, or four antigens for use in the immunoassays of the invention. The invention provides nucleic acid mixtures including nucleic acids for encoding any combination of two, three, or four antigens for use in the immunoassays of the invention.

The test can be used as part of a routine screening panel for HHV-8, a known blood borne pathogen. Due to the inability of PCR to detect the low viral load in blood, the antigen mixture of the instant invention is an alternative providing a rapid, simple, and high-throughput approach for screening for HHV-8 infection or contamination.

In addition to diagnosis of HHV-8 infection, the described HHV-8 antibody test can also have a role in the prognosis and monitoring if HHV-8 associated cancers. For example, one of the new antigens provided herein, HHV-8 v-cyclin, is highly similar to a known human oncogene, cyclin D, which is associated with cancer. Therefore, anti-v-cyclin antibodies may be useful in detection and monitoring of cancer.

Further, the HHV-8 detection method of the invention can be useful for monitoring AIDS disease progression or regression in a subject by detecting the susceptibility to HHV-8 infection.

Further, the method can be used for monitoring donated organs and/or tissues for the presence of HHV-8 infection.

Considerable progress has been made in employing defined recombinant HHV-8 antigens including LANA, K8.1 and ORF65, for testing. The most sensitive ELISAs require separate determinations of 2 or 3 HHV-8 antigens and typically rely on diagnostic algorithms to achieve 90-95% sensitivity and 90-95% specificity at best. Furthermore, one major problem plaguing the assessment of performance of any given HHV-8 serological test is the lack of gold standard reference sera samples. Typically KS patients are available as the only true positives, which may over-estimate the sensitivity of the assay because KS patients generally have much higher antibody titers compared to asymptomatic HHV-8 infected individuals.

Recently, Renilla luciferase (Ruc)-antigen fusions, produced in Cos 1 cells, have been used in an immunoprecipitation assay called LIPS to quantitatively measure antibody responses to cancer-associated autoantigens, autoantigens-associated with autoimmune diseases, and infectious agents including HCV, HIV, HTLV-I, and filarial infections. In this study, we used LIPS to evaluate antigens and potential HHV-8 ORFs for the serological diagnosis of HHV-8 infection. Following the evaluation of pilot and training serum sets, a 4 antigen panel (K8.1, v-cyclin, ORF65, and LANA) was selected. This 4 antigen panel evaluated separately or as a mixture with a validation sera set showed 100% sensitivity and 100% specificity. These results suggest that a LIPS antigen mixture is an efficient high-throughput method for serological screening of HHV-8 infection.

Antibody responses against lytic and latent KSHV antigens were further investigated in patients with Kaposi sarcoma (KS), multicentric Castleman's disease (MCD), and primary effusion lymphoma. Antibodies against the lytic antigen K8.1 were 5-fold higher in MCD than KS patients, while antibodies to the sum of latent antigens v-cyclin and LANA were 27-fold higher in KS compared to MCD patients (P<0.0001). The sum of anti-v-cyclin and anti-LANA antibody titers discriminated patients with KS from those with MCD and KS with 93% sensitivity and 83% specificity. These results suggest that antibody responses to lytic and latent KSHV antigens differ in these diseases.

EXAMPLE 1

Material and Methods

Patient sera for antibody identification. Sera for were obtained from patients or volunteers under institutional review board-approved protocols at the Clinical Center, NIH and at Georgetown University. In the initial pilot set, 6 colon cancer, 15 KS, and one HIV positive sera samples were analyzed. Subsequent analysis of the single HIV positive sample revealed that is was highly positive by both ELISA and LIPS for anti-HHV-8 antibodies and, for simplicity, it was designated as a KS sample making "16" KS samples. The training (n=83 blinded sera) and validation (n=71) sera sample sets were provided as coded samples for both LIPS and ELISA assays and the code was broken only after titers were established and categorization of HHV-8 infection status had been made. The training set consisted of 39 KS samples, while validation set contained 34 KS samples. One volunteer sample in each of the training and validation sets were also found to be HHV-8 positive by both ELISA and LIPS and these samples are denoted by a triangle in the figures.

Patient sera for characterization of HHV-8 associated disease antibodies. Sera were from patients or volunteers under institutional review board-approved protocols at the NIH Clinical Center, NIAID, and the NCI. Serum samples from 35 patients with KS, 14 with both MCD and KS (MCD+/KS+), 6 with MCD but no KS (MCD+/KS−), and 5 with PEL, all generally taken at the time of diagnosis, and 34 KSHV-uninfected controls were tested. The median CD4 counts for KS ($270/mm^3$, interquartile range (IQR) 137-530), MCD+/KS+ ($294/mm^3$, IQR 185-620) and MCD+/KS− ($359/mm^3$, IQR 123-580) were not statistically different between the paired groups. The PEL patients had the lowest median CD4 counts ($111/mm^3$, IQR 46-368) and were statistically lower only to the MCD+/KS+ samples.

HHV-8 ELISA. Anti-HHV-8 antibodies were determined using two different ELISAs employing baculovirus-produced LANA (ORF73) and bacterially-produced K8.1 antigen as described (Burbelo et al., 2008 *Diabetes care* 31:1824-1826).

Generation of Ruc-antigen fusion constructs. pREN2, a mammalian Renilla luciferase (Ruc) expression vector, was used to generate all plasmids (Burbelo et al., *BMC Biotechnol* 2005;5:22). HHV-8 clones were amplified by PCR specific linker-primer adapters using HHV-8 genomic DNA and a LANA cDNA template. Using gene-specific primer in PCR amplifications, the full-length coding sequences, as well as sub-fragments were generated for fusions at the C-terminus of Ruc. For each construct, including deletion mutants, a stop codon was included at the end of the coding sequence. The primer adapter sequences used to clone each protein or protein fragment are available on request. DNA sequencing was used to confirm the integrity of all the DNA constructs. Plasmid DNA was then prepared from the different pREN2 expression vectors using a Qiagen Midi preparation kit.

Figure 4:
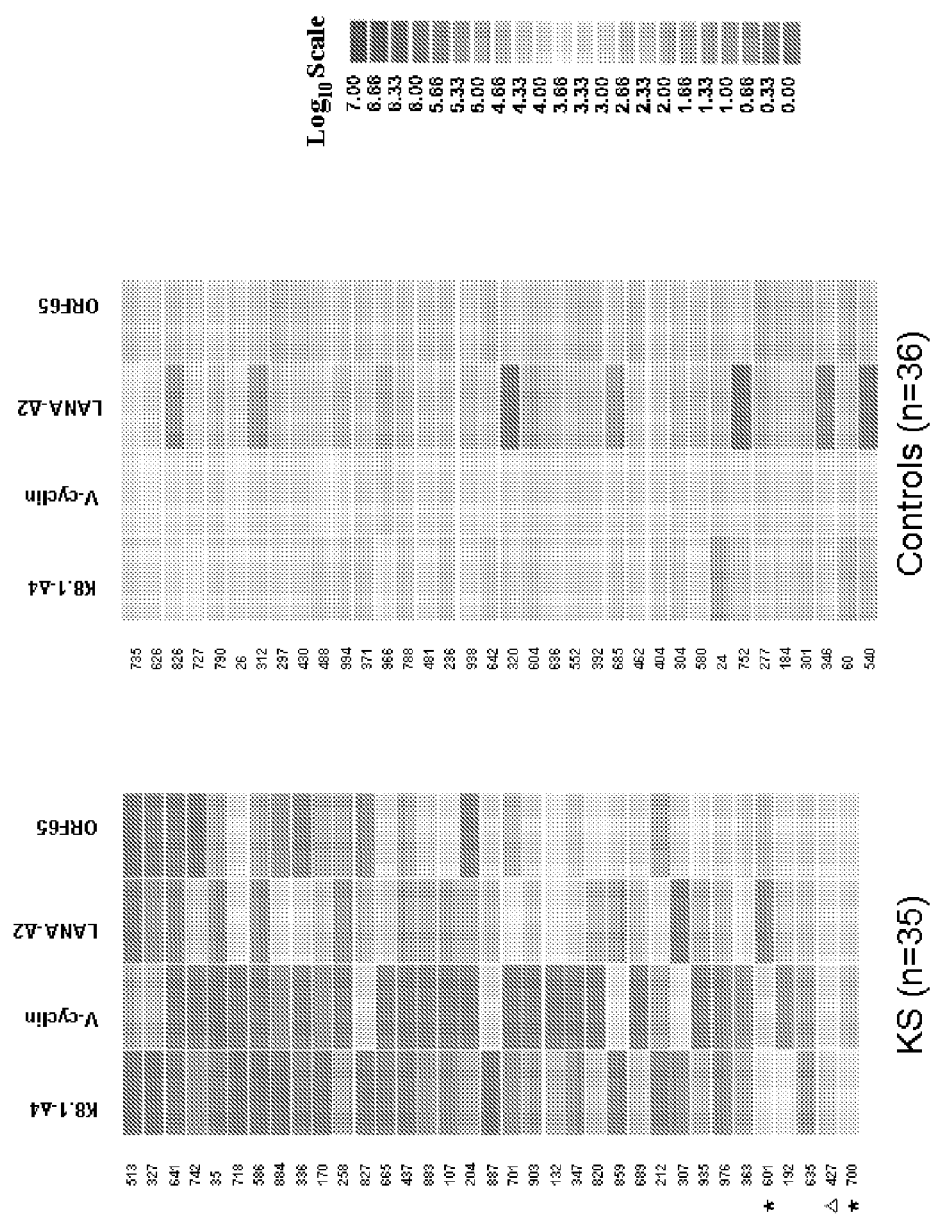
FIG. 4. Heat map representation of patient antibody profiles to the 4 HHV8 antigens. The titer values for each serum were $\log^{10}$ transformed and then the titer levels were coded as indicated by the $\log^{10}$ scale on the left, in which signal intensities shown in greyscale indicate high (darker grey) and low (lighter grey) titers. The samples were rank ordered from highest to lowest based on the sum of the antibody titers to the 4 antigen panel. The samples on the left are from HHV-8 infected sera. The asterisk marks the samples that were negative or indeterminate for anti-K8.1 and anti-LANA antibodies by ELISA. A volunteer sample (non-KS) from the validation cohort found HHV-8 positive by both ELISA and LIPS is denoted by the triangle.

LIPS analysis. Following transfection of mammalian expression vectors, crude protein extracts were obtained as described (Burbelo et al., *Biochem Biophys Res Commun* 2008;366:1-7). The LIPS immunoprecipitation assay was performed in a 96-well plate format at room temperature using a robotic workstation (Burbelo et al. *Diabetes Care* 2008;3 1:1824-6). All light units (LU) data for the training and validation cohorts were obtained from the average of two separate experiments and corrected for background by subtracting the LU values of beads incubated with Cos1 cell extract, but without sera. In addition to the individual tests, the combined sum values of the separate antigen tests were also calculated. The data presented in FIG. 4 are $\log^{10}$ transformed values and coded using a color palette ranging from red to green indicating high and low titers, respectively.

For the antigen mixture tests, the assay was modified slightly. In these tests, the Ruc-antigen extracts were harvested in lysis buffer without glycerol and used immediately upon collection. Four to six antigens mixtures were added to each well and processed as above.

Data analysis. The GraphPad Prism software (San Diego, Calif.) was used for statistical analysis. Results for qualitative antibody titers between the controls and KS individuals are reported as the mean+standard deviation (SD). Mann-Whitney U tests were used to compare the antibody titers among the groups. For the calculation of sensitivity and specificity, a cut-off limit of approximately 9,000 LU was used, which was derived from the combined value of the mean value of the 6 control samples plus 5 standard deviations for each antigen from the pilot set.

EXAMPLE 2

Patient Antibody Responses to Known HHV-8 Antigens

Evaluation of the utility of LIPS in HHV-8 diagnosis began by screening sera samples from 16 KS and 6 control patients for antibodies against known HHV-8 antigens, including LANA, ORF65 and K8.1. Because of the small pilot set, the discriminatory potential of each of these HHV-8 antibody tests was evaluated by a variety of statistical and diagnostic methodology including receiver operator characteristics (ROC), area under the curve (AUC), Whitney-Mann U tests and using sensitivity and specificity calculations derived from the mean plus 5 SD of the control samples (Table 1).

In the case of LANA, we generated three different protein fragments designated LANA-Δ1, LANA-Δ2, and LANA-Δ3, respectively. Using the N-terminal LANA-Δ1 fragment, only one of the 16 KS sera showed positive results by the cut-off compared to the controls (Table 1). In contrast, LANA-Δ2, representing the central region of LANA, detected positive antibody responses in 10 of 16 KS sera and none of the 6 controls (Table 1). The LANA-Δ3 fragment, representing the C-terminus of LANA, performed slightly better than the LANA-Δ2 and reacted with 13 of the 16 KS samples (Table 1). Several other larger LANA constructs did not increase the diagnostic sensitivity of the LIPS test over the values obtained with the LANA-Δ2 and LANA-Δ3 fragments (data not shown).

Analysis of full-length ORF65 by LIPS correctly identified 10 of 16 KS samples and showed no immunoreactivity in the controls (Table 1). Initial tests of K8.1 utilized two different K8.1 exon fragments. Both these protein fragments, K8.1-Δ1 (containing 123 amino acid residues) and K8.1-Δ2 (containing 89 amino acids) identified the same 12 KS samples as positive (Table 1 and data not shown). Subsequent testing of K8.1-Δ4, containing the complete coding sequence of the K8.1 protein, demonstrated diagnostic superiority in comparison to the two smaller K8.1 fragments and detected 13 of 16 KS samples (Table 1).

EXAMPLE 3

Identification of v-cyclin as a New Informative HHV-8 Antigen

To identify potentially new HHV-8 antigens, the pilot sera set was screened with a panel of 14 different HHV-8 fusion proteins including v-cyclin, vFLIP/ORF71/K13, v-BCL2/ORF16,vIL-6/K2, v-GPCR/Orf74, ORF48, ORF52, Kaposin/K12, ORF57, vIRF-1/ORF K9, vIRF-3/LANA2, ORF45, ORF47 and MCP-1 Most of these HHV-8 proteins showed weak or non-existent antibody signals with the KS sera (Table 1 and data not shown). For example, ORF52 showed weak positive signals in only 3 of the 16 KS sera (Table 1), while ORF74 showed no signal in any of the sera tested (data not shown). However, the latent HHV-8 protein, v-cyclin, displayed positive results in 12 of 16 KS samples (Table 1). The geometric mean titer of the anti-v-cyclin antibody in the 16 KS samples was 14,281 LU (95% CI, 1,318-

154,759 LU), 1000 fold higher than the geometric mean titer of 15 LU (95% confidence interval [CI], 0.65-56) in the controls (Mann Whitney U test, P<0.0068). The anti-v-cyclin antibody positive KS patients did not simply reflect high anti-HHV8 antibody responding patients, as 2 of 16 anti-v-cyclin positive samples were from KS sera that were negative for anti-LANA, anti-K8.1, and anti-ORF65 antibodies. These results demonstrate that anti-v-cyclin antibodies represent a highly sensitive, independent marker of HHV-8 infection in KS patients.

EXAMPLE 4

Selection of a HHV-8 Antigen Panel

We focused our efforts on defining a diagnostic antigen panel and utilized the six most informative antigens: LANA-Δ2, LANA-Δ3, v-cyclin, K8.1-Δ1, K8.1-Δ2 and ORF65 with sensitivity values of 63%, 81% 75%, 75%, 75%, and 63%, respectively. We derived a cut-off value of 9,000 LU from the approximate sum of the values of the mean plus 5 SD. Using this parameter and the combined results of each singly tested antigen, LIPS correctly identified 15 of the 16 KS patient sera (94% sensitivity and 100% specificity). This panel missed only one KS patient sample, later identified as an individual with a low CD4 count of 40. In comparison, the HHV-8 ELISA, based on two separate LANA and K8.1 tests, detected 13 of the 16 KS samples as positive (81% sensitivity and 100% specificity), with 3 KS samples designated as indeterminate. Interestingly, one of the ELISA indeterminate sera was also the same serum sample missed by LIPS.

EXAMPLE 5

Initial Testing of the Training Set With an HHV-8 Panel

Based on the results of the pilot set, an independent training set of 83 blinded sera was tested with the 6 antigen panel identified above. We screened the six antigens separately and also simultaneously as a single antigen mixture.

Figure 1:
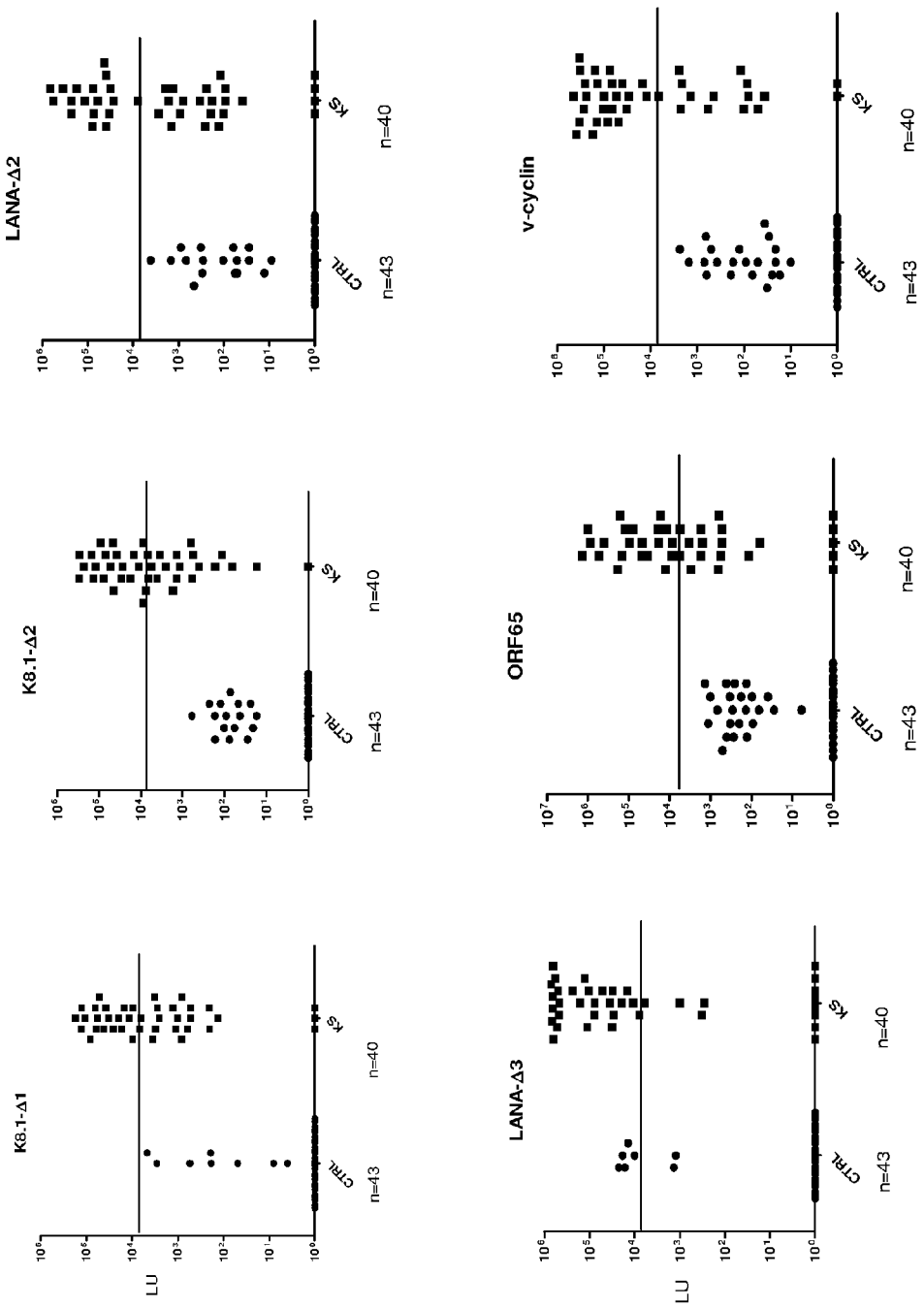
FIG. 1. LIPS detection of antibodies to 6 six different HHV-8 protein fragments. Using LIPS, antibodies were evaluated against K8.1-Δ1, K8.1-Δ2, LANA-Δ2, LANA-Δ3, v-cyclin and ORF65 using 83 sera from a training set. Each symbol represents individual samples from the training set consisting of 43 controls and 40 KS/HHV-8-infected subjects. Antibody titers in LU are plotted on the Y-axis using a $\log^{10}$ scale. The 9,000 LU cut-off is shown by the solid line. A volunteer sample (non-KS) from the training cohort found HHV-8 positive by both ELISA and LIPS is denoted by the triangle.

The sum of the 6 separate tests and the value of the 6 antigen mixture closely correlated (Pearson R=0.97, p<0.00001), and using the 9,000 LU cutoff, both formats identified the same 44 potential positives. Following unblinding, LIPS performance showed 95% sensitivity (38/40) and 88.4% specificity (38/43). In addition, all 6 separate tests showed robust antibody titers in many of the KS samples compared to the volunteers (FIG. 1). Compared to LIPS, the optimized ELISA showed slightly higher performance of 97.5% (39/40) sensitivity and 88.4% (38/43) specificity.

EXAMPLE 6

Improving the Performance of the HHV-8 Antigen Panel

Figure 2:
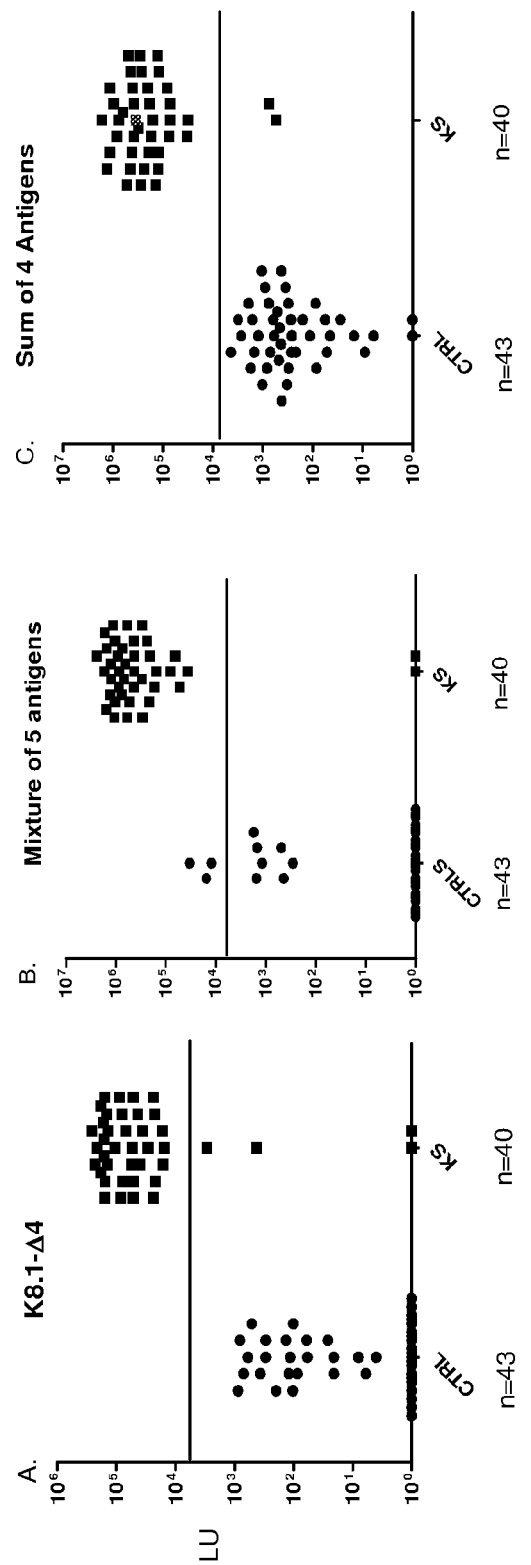
FIG. 2. Improving the performance of the LIPS test. The 83 sera of the training set were re-blinded and retested with a new 5 antigen mixture employing K8.1-Δ4 instead of K8.1-Δ1 and K8.1-Δ2 (A), as well as with K8.1-Δ4 alone (B). Use of the same cut-off of 9,000 LU with the new 5 antigen mixture resulted in improved diagnostic performance of 95% (38/40) sensitivity and 93% (40/43) specificity. The sum antibody titers to only 4 antigens (LANA-Δ2, K8.1-Δ4, v-cyclin and ORF65) was recalculated (C) and using the 9,000 LU cut-off with these 4 antigens markedly improved the test (95% sensitivity and 100% specificity). A volunteer sample (non-KS) from the training cohort found HHV-8 positive by both ELISA and LIPS is denoted by the triangle.

During the course of our studies, a new K8.1 antigen, K8.1-Δ4, was found to have the highest discriminatory potential in comparison to other HHV-8 antigens (Table 1). In an effort to improve the performance of the HHV-8 LIPS panel, we replaced K8.1-Δ1 and K8.1-Δ2 protein fragments with the full length K8.1-Δ4. After re-blinding the 83 sera from the training set, we reevaluated the sera by LIPS using this new 5 antigen mixture (K8.1-Δ4, v-cyclin, LANA-Δ2, LANA-Δ3 and ORF65). Following unblinding, the results showed that the 5 antigen panel improved diagnostic performance, demonstrating 95% (38/40) sensitivity and 93% (40/43) specificity (FIG. 2A). Particularly promising was the finding that the anti-K8.1-Δ4 test independently detected all but 4 of the 40 KS samples (90% sensitivity) with 100% specificity (FIG. 2B). Despite the improved performance of this new 5 antigen mixture, 3 false positive sera were still found above cut-off of 9,000 LU. Inspection of the separate results from these 5 antigen tests revealed that the LANA-Δ3 test was responsible for all the false samples above the 9,000 LU cut-off. Since the anti-LANA-Δ3 antibody positives signals were also positive for anti-LANA-Δ2 antibody test, we omitted the LANA-Δ3 result and recalculated the sum of the 4 antigen tests (LANA-Δ2, K8.1-Δ4, v-cyclin, and ORF65). This new 4 antigen panel showed 95% sensitivity and 100% specificity for discriminating HHV-8 positive from negative samples (FIG. 2C). These results suggest that this 4 antigen panel assayed separately or potentially as a mixture might be a simple and useful test for diagnosis.

EXAMPLE 7

A Four HHV-8 Antigen Panel Shows 100% Sensitivity and 100% Specificity

Figure 3:
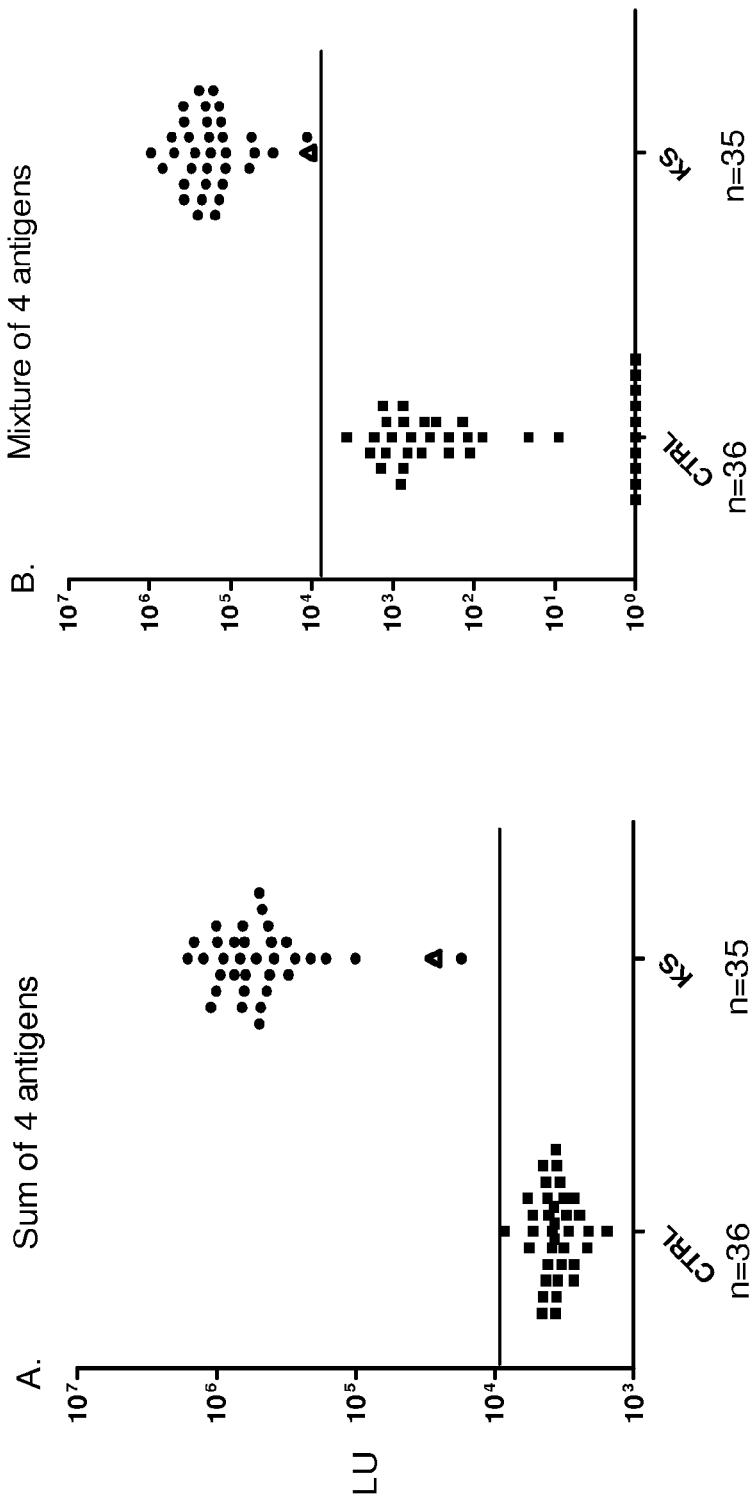
FIG. 3. A four HHV-8 antigen panel shows 100% sensitivity and 100% specificity. Antibodies were evaluated by LIPS with a 71 sera validation cohort using a 4 antigen panel consisting of K8.1-Δ4, LANA-Δ2, v-cyclin and ORF65. These LIPS tests were either evaluated separately and summed (A) or tested as a cocktail (B). As shown, both tests showed similar results and had 100% sensitivity and specificity. The 9,000 LU cut-off is shown by the solid line. A volunteer sample (non-KS) from the validation cohort found HHV-8 positive by both ELISA and LIPS is denoted by the triangle.

To test the effectiveness of this new 4 antigen panel, a new validation cohort of 71 blinded sera were evaluated with the 4 antigens individually and as a mixture. The 4 HHV-8 antigens assayed separately or as a mixture perfectly distinguished (100% sensitivity and 100% specificity) the 35 HHV-8 positive samples from the 36 controls (FIG. 3). The sum of the 4 separate tests and as a 4 antigen mixture also closely correlated (Pearson R=0.95, p<0.00001). LIPS also detected two more positive samples compared to the ELISA (94% sensitivity and 100% specificity), but ROC analysis of LIPS and ELISA showed no significant difference in diagnostic performance.

Further analysis of anti-K8.1, anti-v-cyclin, anti-LANA-Δ2 and anti-ORF65 antibody titers measured by LIPS in the above assays revealed that the patient antibody responses to these different antigens markedly varied. For example, using the Spearman Rank test, the correlation between the anti-K8.1 and anti-v-cyclin antibodies was R=-0.13 (95% CI, -0.4511 to 0.2237), while the correlation of anti-cyclin and anti-LANA antibodies was R=0.06 (95% CI, -0.2861 to 0.3964). To easily visualize these differing patient antibody responses toward the panel of 4 HHV-8 antigens, a heat map was employed (FIG. 4). In this graphical format, the marked differences in patient antibody responses to this panel become obvious. For example, several samples including 513, 327 and 35 showed high level of antibodies to all four antigens, while several samples including samples 192, 635 and 700 showed only weak antibodies to one or two antigens. Of note one of the KS patients, sample 700, only had significant anti-v-cyclin antibodies and was missed by the ELISA (FIG. 4).

The differences observed in antigen binding are a result of a number of factors including, but not limited to, differences in HLA types of subjects and length of HHV-8 infection from which the samples are obtained. Therefore, it is expected that not all subject sera will bind to the same antigens in spite of being exposed to the same antigens from HHV8. The incorporation of these 4 antigens into a single assay increases the probability that an HHV-8 infected individual will be detected.

EXAMPLE 8

Figure 5:
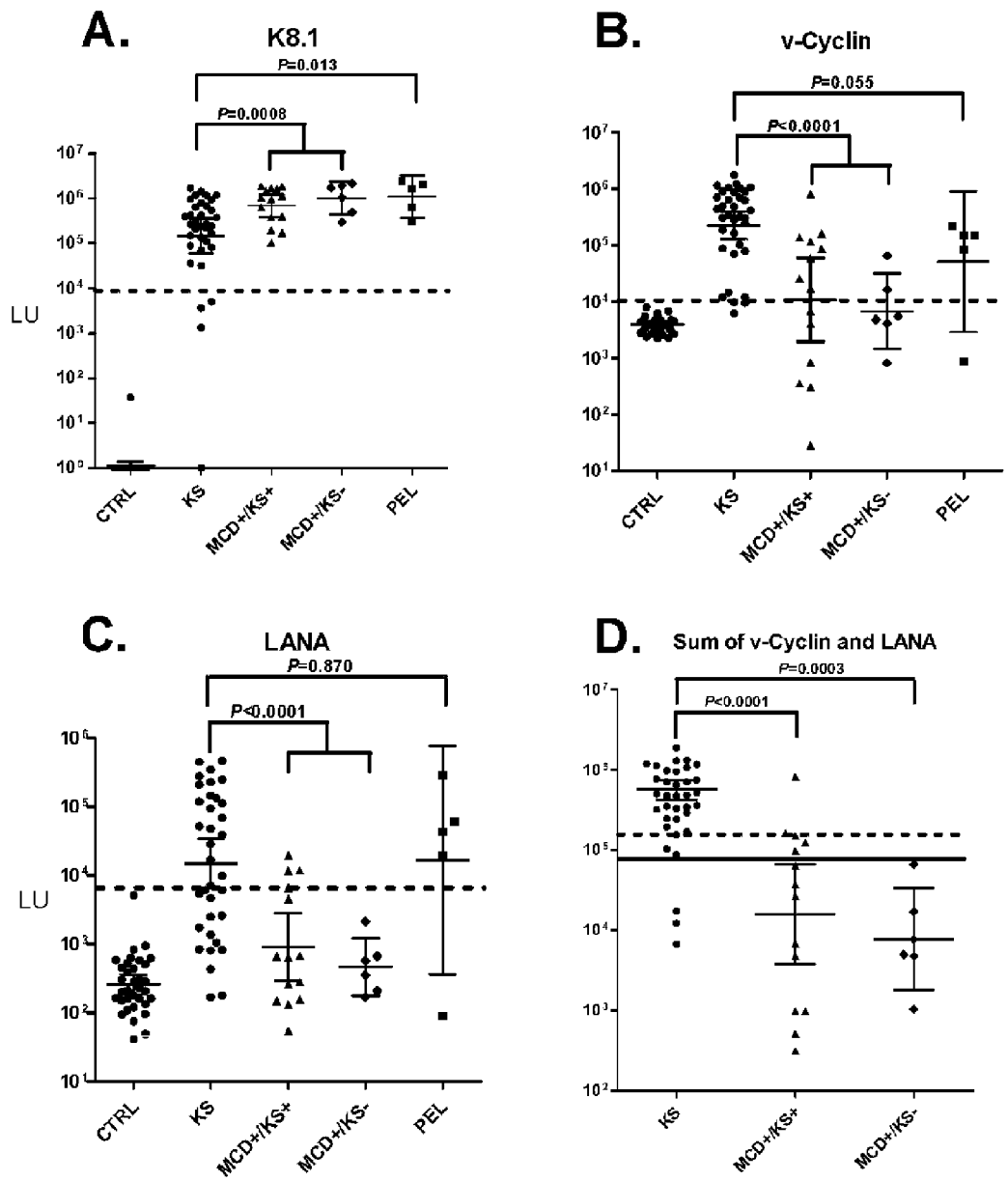
FIG. 5A-D. Anti-K8.1, anti-v-Cyclin and anti-LANA antibodies in uninfected controls, KS, MCD and PEL patients.

Identification of Antibodies to Differentiate Kaposi Sarcoma, Multicentric Castlemen's Disease, and Primary Effusion Lymphoma Using the LIPS assay and antigens from both the lytic and latent phase of the KSHV life cycle, we compared antibody responses among the patient cohorts. The GMT of antibodies to K8.1 early lytic antigen was 145,900 LU (95% CI; 58,490-363,700) in the 35 KS patients, 684,700 LU (95% CI: 390,100-1,202,000) in the 14 MCD/KS+patients, 1,020,000 LU (95% CI; 437,500-2,378,000) in the 6 MCD/KS−, and 1,092,000 LU (95% CI; 366,600-3,252,000) in the 5 PEL patients (FIG. 5A). Statistical analysis using the Mann Whitney U test revealed that KS patients had significantly lower anti-K8.1 antibody titers than MCD/KS+ (P=0.009), MCD/KS− (P=0.008) or the PEL patients (P=0.013). Also, the difference between the anti-K8.1 antibody titers in KS versus the combined MCD/KS+ and MCD/KS− patient groups was highly significant (P=0.0008).

The GMT of the late lytic antigen, ORF65, in the 35 KS patients was 34,380 LU (95% CI; 12,570-94,050) and was significantly lower (P<0.006) than the GMT of 1,010,000 LU (95% CI; 317,300-3,214,000) for the PEL patients (data not shown). The MCD+/KS+ and MCD+/KS− patients showed variable antibody titers and were not significantly different from the KS patients (data not shown).

Antibody titers were also evaluated against two latent antigens, v-cyclin and LANA (ORF73). The anti-v-cyclin in GMT in the KS patients was 225,900 LU (95% CI; 128,600-396,900), which was markedly higher than the GMT of 10,840 LU (95% CI: 1964-59,840) in the MCD+/KS+ patients (P=0.0004) or 6,751 LU (95% CI; 1446-31,530) for the MCD+/KS− patients (P=0.0006). As shown in FIG. 5B, the difference between the anti-v-cyclin antibody titers in KS versus the combined MCD/KS+ and MCD/KS− patient groups was also highly significant (P<0.0001). The GMT for the PEL patients was 51,563 LU (95% CI; 2943-903,400) which trended lower than the GMT for the KS patients (P=0.055). Using a cutoff value based on the uninfected controls, 91.4% (32/35) of the KS, 71.4% (10/14) of the MCD+/KS+, 40% (2/5) of the MCD+/KS−, and 80% (4/5) of the PEL patients were seropositive for anti-v-cyclin antibodies.

As shown in FIG. 5C, antibodies against the latent protein, LANA, in the KS patients showed a GMT of 14,940 LU (95% CI; 6520-34,250). Lower levels of anti-LANA antibodies were found in the MCD+/KS+ patients with a GMT of 907 LU (95% CI: 292-2823) and the MCD+/KS− patients with a GMT of 465 LU (95% CI; 177-1218) (FIG. 5C). Significant differences were found between the anti-LANA antibodies in KS versus the MCD+/KS+ (P=0.0007) and MCD+/KS− (P=0.002). Additionally, the difference between the anti-LANA antibody titers in KS versus the combined MCD/KS+ and MCD/KS− patient groups was highly significant (P<0.0001). The PEL patients showed high anti-LANA antibodies, which were not significantly different from the KS patients (P=0.87). Using a cut-off derived from the uninfected controls (FIG. 5C), 63% (22/35) of KS patients were positive versus 80% (4/5) of the PEL, 21% (3/14) of the MCD+/KS+, and none (0/6) of the MCD+/KS− patients. These results suggest that the relative absence of anti-LANA antibodies is a common feature of MCD compared to patients with KS or PEL.

The titer data were also analyzed to determine whether any single antibody or antibody combination might distinguish KS from those with MCD+/KS+ and/or MCD+/KS−. In part because the anti-LANA and anti-v-cycl in antibody titers in the KS patients tracked each other poorly (rs=0.03), even greater antibody titer differences were observed in the patient groups using the sum of the anti-v-cyclin and anti-LANA antibodies. Specifically, the sum of the anti-v-cyclin and anti-LANA antibodies was 350,700 LU (95% CI; 223,700-550,000) in the 35 KS patients, 15,880 LU (95% CI: 3746-67,330) in the 14 MCD/KS+ patients, and 7,686 LU (95% CI; 1783-33,130) in the 6 MCD/KS− (FIG. 5D). As shown in FIG. 5D, significant differences were found between the sum of the anti-v-cyclin and anti-LANA antibodies in KS versus the MCD+/KS+ (P<0.0001) and MCD+/KS− (P=0.0003). Also, the difference between the sum of the antibody titers in KS versus the combined MCD/KS+ and MCD/KS− patient groups was highly significant (P<0.0001). From receiver operator characteristics the most informative approach to optimally separate the KS and from the MCD+/KS− patients used the sum of these latent antigens with a cut-off of 70,000 LU and discriminated KS from MCD+/KS− with 100% sensitivity and 91% specificity (FIG. 5D). Although this 70,000 LU cut-off was less useful in discriminating KS from MCD+/KS+ (64% sensitivity and 91% specificity), a higher cut-off of 165,000 LU showed 93% sensitivity (13/14 of the MCD+/KS+ were below the cut-off) and 83% specificity for distinguishing KS from MCD+/KS+ (FIG. 5D).

By profiling antibodies against several latent and lytic HHV-8 antigens, significant differences in antibody titers were observed between the KS, MCD and PEL patients. One of the most obvious differences was that antibody titers against the early lytic HHV-8 antigen, K8.1, were markedly higher in the PEL and MCD patients compared to the KS patients. The findings of higher anti-K8.1 in MCD are consistent with studies showing that a substantial percentage of MCD cells express lytic KSHV genes, including a virally-encoded IL-6. Similarly, the higher antibody titers against the ORF65 lytic protein in PEL as compared to KS may also reflect the greater KSHV viral load and expression of lytic antigens in PEL. It is not clear why antibodies to another lytic antigen, ORF65, were not significantly higher in MCD than in KS. It is possible that it relates to ORF65 being a late lytic antigen. Alternatively, it is possible that this is in part because MCD patients have some subtle defects in specific antibody production, perhaps related to cytokine dysregulation that blunts what would otherwise be an increase.

By contrast to the anti-K8.1 antibody profile, markedly higher antibodies to v-cyclin, a latent KSHV gene, were found in the KS and PEL patients compared to the MCD. Anti-LANA antibodies also were also markedly higher in the KS compared to the MCD patients. Together these results are consistent with immunohistochemical studies showing that KS spindle cells express large amounts of latent HHV-8 proteins compared to MCD cells. At present, we have no definitive explanation for why MCD+/KS+ patients have lower antibody titers to v-cyclin and LANA compared to patients with only KS. Relatively greater HIV-induced immunosuppression in the MCD patients does not seem to be the cause because the CD4 counts were similar in the KS, MCD+/KS+ and MCD+/KS− groups. As noted above, it is possible that MCD patients have a blunting of specific antibody responses to KSHV antigens, perhaps related to local cytokine dysregulation.

Since elevated anti-latent antibodies are a common feature found of KS patients compared to MCD, the sum of the anti-v-cyclin and anti-LANA antibodies was the most useful approach for optimally separating KS from MCD+/KS+ and MCD+/KS−. Using this approach with a cut-off value of 165,000 LU discriminated KS from MCD+/KS+ with 93% sensitivity and 83% specificity. This and other KSHV antibody tests may be useful in identifying KS patients who may also have developed MCD, a disease that can be difficult to diagnose. Possible explanations for the higher anti-latent antibody responses in KS as compared to MCD+/KS+ and MCD+/KS− may include greater expression of KSHV latent antigens in KS or possibly blunting of KSHV-specific antibody formation in MCD as postulated above. In summary, antibody responses to latent and lytic KSHV proteins are different between KS, MCD+/KS+, MCD+/KS− and PEL patients and likely reflect altered protein expression and/or immune recognition differences among these diseases.

All references, patents, patent applications, and GenBank numbers as of the date of filing of the instant application are hereby incorporated by reference as if they were each incorporated individually.

TABLE 1

Performance of Top 10 HHV-8 Antigens for KS Diagnosis

| Name | AUC | P value | Sensitivity | Specificity |
|---|---|---|---|---|
| K8.1-Δ4 | 0.96 | 0.0011 | 13/16 | 0/6 |
| K8.1-Δ1 | 0.92 | 0.0028 | 12/16 | 0/6 |
| LANA-Δ3 | 0.91 | 0.0052 | 13/16 | 0/6 |
| v-Cyclin | 0.89 | 0.0068 | 12/16 | 0/6 |
| ORF65 | 0.84 | 0.0105 | 10/16 | 0/6 |
| LANA-Δ2 | 0.82 | 0.0212 | 10/16 | 0/6 |
| K8.1-Δ2 | 0.81 | 0.0271 | 12/16 | 0/6 |
| ORF-52 | 0.58 | 0.5669 | 3/16 | 1/6 |
| ORF-47 | 0.55 | 0.7667 | 1/16 | 0/6 |
| LANA-Δ1 | 0.52 | 0.8530 | 1/16 | 0/6 |

[1]Receiver operator characteristic as determined by area under curve (AUC).
[2]The P value was calculated by Mann Whitney U test
[3]For LIPS, the cut-off limit for calculating sensitivity and specificity for each antigen was derived from the value of the mean plus 5 SD of the 6 control samples.

TABLE 2

HHV-8 peptide fragments

| Name | SEQ ID NO: | Fragment (aa) | GenBank Acc. | Sensitivity/Specificity |
|---|---|---|---|---|
| K8.1-Δ1 | 1 | 1-141 | YP_001129404 | Good |
| K8.1-Δ2 | 1 | 143-228 | YP_001129404 | Good |
| K8.1-FL | 1 | 2-228 | YP_001129404 | Good |
| K8.1-Δ4[1] | 1 | 25-228 | YP_001129404 | Excellent |
| ORF65[2] | 2 | 2-170 | YP_001129422 | Excellent |
| v-Cyclin[3] | 3 | 2-257 | YP_001129430 | Excellent |
| LANA-Δ1 | 4 | 6-286 | YP_001129431 | Good (false positives) |
| LANA-Δ2[4] | 4 | 274-925 | YP_001129431 | Excellent |
| LANA-Δ3 | 4 | 863-1129 | YP_001129431 | Poor |
| LANA-Δ4 | 4 | 6-925 | YP_001129431 | Good |
| LANA-Δ5 | 4 | 58-286 | YP_001129431 | Good |
| LANA-Δ6 | 4 | 58-925 | YP_001129431 | Good |

[1]Also SEQ ID NO: 5
[2]Also SEQ ID NO: 6
[3]Also SEQ ID NO: 7
[4]Also SEQ ID NO: 8

We claim:

1. A method of detecting active, latent, or prior HHV8 infection of a subject sample, comprising:
   providing a subject sample;
   contacting the subject sample with at least an antigenic fragment of an HHV-8 v-cyclin polypeptide (SEQ ID NO: 3), wherein the antigenic fragment is covalently linked to a reporter polypeptide, and comprises an HHV-8 v-cyclin epitope;
   detecting specific binding of an antibody in the sample that specifically binds to the antigenic fragment of the HHV-8 v-cyclin by detecting the reporter polypeptide;
   wherein the specific binding of an antibody to the antigenic fragment of the HHV-8 v-cyclin indicates an HHV-8 infection of the subject.

2. The method of claim 1, wherein the antigenic fragment of v-cyclin comprises a polypeptide comprising the sequence of at least amino acids 2 to 257 of SEQ ID NO: 3.

3. The method of claim 1, further comprising contacting the subject sample with at least an antigenic fragment of at least one of an HHV-8 K8.1 polypeptide (SEQ ID NO: 1), an HHV-8 ORF65 polypeptide (SEQ ID NO: 2), and an HHV-8 LANA polypeptide (SEQ ID NO: 4), wherein said fragment comprises an epitope of said polypeptide, and further comprising detecting specific binding of an antibody in said sample to said fragment(s).

4. The method of claim 1, wherein the method further comprises contacting the subject sample with at least an antigenic fragment of at least two of an HHV-8 K8.1 polypeptide (SEQ ID NO: 1), an HHV-8 ORF65 polypeptide (SEQ ID NO: 2), and an HHV-8 LANA polypeptide (SEQ ID NO: 4), wherein said fragment comprises an epitope of said polypeptide, and further comprising detecting specific binding of an antibody in said sample to said fragment(s).

5. The method of claim 1, wherein the method further comprises contacting the subject sample with at least an antigenic fragment of at least three of an HHV-8 K8.1 polypeptide (SEQ ID NO: 1), an HHV-8 ORF65 polypeptide (SEQ ID NO: 2), and an HHV-8 LANA polypeptide (SEQ ID NO: 4), wherein said fragment comprises an epitope of said polypeptide, and further comprising detecting specific binding of an antibody in said sample to said fragment(s).

6. The method of claim 3, wherein the antigenic fragment of HHV-8 K8.1 polypeptide (SEQ ID NO: 1) comprises a polypeptide sequence selected from the group consisting of: amino acids 25-228, amino acids 143-228, amino acids 2-228, amino acids 1-141, and amino acids 25-141 of SEQ ID NO: 1.

7. The method of claim 3, wherein at least an antigenic fragment of ORF65 polypeptide (SEQ ID NO: 3) comprises the polypeptide sequence of amino acids 2-170 of SEQ ID NO: 3.

8. The method of claim 3, wherein at least an antigenic fragment of HHV-8 LANA polypeptide (SEQ ID NO: 4) comprises a polypeptide sequence selected from amino acids 274-925, amino acids 6-286, amino acids 6-925, amino acids 58-286, amino acids 58-925, amino acids 286-925, amino acids 286-863, amino acids 6-863, and amino acids 58-863 of SEQ ID NO: 4.

9. The method of claim 3, wherein contacting a sample with at least two antigenic fragments of at least two HHV-8 polypeptides is performed in a single reaction.

10. The method of claim 4, wherein contacting a sample with at least three antigenic fragments of at least three HHV-8 polypeptides is performed in a single reaction.

11. The method of claim 5, wherein contacting a sample with at least four antigenic fragments of at least four HHV-8 polypeptides is performed in a single reaction.

12. The method of claim 1, wherein the sample is contacted with two antigenic fragments of HHV-8 v-cyclin.

13. The method of claim 3, wherein the antigenic fragment is selected from the group consisting of: HHV-8 LANA-Δ2 (SEQ ID NO: 8), HHV-8 K8.1-Δ4 (SEQ ID NO: 5), and HHV-8 ORF65 fragment (SEQ ID NO: 6).

14. The method of claim 1, further comprising identifying a subject having or suspected of having an HHV8 infection.

15. The method of claim 1 in a subject identified as having an HHV-8 infection, further comprising comparing an amount of antibody bound to an antigenic fragment of v-cyclin or an antigenic fragment of LANA to an amount of antibody bound to an antigenic fragment of ORF65, wherein a greater amount of antibody binding to an antigenic fragment of v-cyclin or an antigenic fragment of LANA relative to an antigenic fragment of ORF65 indicates a lytic HHV-8 infection; and a greater amount of antibody binding to an antigenic fragment of ORF65 relative to an antigenic fragment of v-cyclin or an antigenic fragment of LANA indicates a latent infection in the subject.

16. The method of claim 1, wherein the subject has not been diagnosed with Kaposi's sarcoma.

17. The method of claim 1, wherein the antigenic fragment of HHV-8 v-cyclin is SEQ ID NO: 7.

* * * * *

```
SEQUENCE LISTING

<160> NUMBER OF SEQ ID NOS: 16

<210> SEQ ID NO 1
<211> LENGTH: 228
<212> TYPE: PRT
<213> ORGANISM: human herpesvirus 8

<400> SEQUENCE: 1

Met Ser Ser Thr Gln Ile Arg Thr Glu Ile Pro Val Ala Leu Leu Ile
1               5                   10                  15

Leu Cys Leu Cys Leu Val Ala Cys His Ala Asn Cys Pro Thr Tyr Arg
            20                  25                  30

Ser His Leu Gly Phe Trp Gln Glu Gly Trp Ser Gly Gln Val Tyr Gln
        35                  40                  45

Asp Trp Leu Gly Arg Met Asn Cys Ser Tyr Glu Asn Met Thr Ala Leu
    50                  55                  60

Glu Ala Val Ser Leu Asn Gly Thr Arg Leu Ala Ala Gly Ser Pro Ser
65                  70                  75                  80

Ser Glu Tyr Pro Asn Val Ser Val Ser Val Glu Asp Thr Ser Ala Ser
                85                  90                  95

Gly Ser Gly Glu Asp Ala Ile Asp Glu Ser Gly Ser Gly Glu Glu Glu
            100                 105                 110

Arg Pro Val Thr Ser His Val Thr Phe Met Thr Gln Ser Val Gln Ala
        115                 120                 125

Thr Thr Glu Leu Thr Asp Ala Leu Ile Ser Ala Phe Ser Gly Ser Tyr
    130                 135                 140

Ser Ser Gly Glu Pro Ser Arg Thr Thr Arg Ile Arg Val Ser Pro Val
```

```
                145                 150                 155                 160
Ala Glu Asn Gly Arg Asn Ser Gly Ala Ser Asn Arg Val Pro Phe Ser
                165                 170                 175

Ala Thr Thr Thr Thr Thr Arg Gly Arg Asp Ala His Tyr Asn Ala Glu
                180                 185                 190

Ile Arg Thr His Leu Tyr Ile Leu Trp Ala Val Gly Leu Leu Leu Gly
                195                 200                 205

Leu Val Leu Ile Leu Tyr Leu Cys Val Pro Arg Cys Arg Arg Lys Lys
                210                 215                 220

Pro Tyr Ile Val
225

<210> SEQ ID NO 2
<211> LENGTH: 170
<212> TYPE: PRT
<213> ORGANISM: human herpesvirus 8

<400> SEQUENCE: 2

Met Ser Asn Phe Lys Val Arg Asp Pro Val Ile Gln Glu Arg Leu Asp
1               5                   10                  15

His Asp Tyr Ala His His Pro Leu Val Ala Arg Met Asn Thr Leu Asp
                20                  25                  30

Gln Gly Asn Met Ser Gln Ala Glu Tyr Leu Val Gln Lys Arg His Tyr
            35                  40                  45

Leu Val Phe Leu Ile Ala His His Tyr Tyr Glu Ala Tyr Leu Arg Arg
        50                  55                  60

Met Gly Gly Ile Gln Arg Arg Asp His Leu Gln Thr Leu Arg Asp Gln
65                  70                  75                  80

Lys Pro Arg Glu Arg Ala Asp Arg Val Ser Ala Ser Ala Tyr Asp
                85                  90                  95

Ala Gly Thr Phe Thr Val Pro Ser Arg Pro Gly Pro Ala Ser Gly Thr
            100                 105                 110

Thr Pro Gly Gly Gln Asp Ser Leu Gly Val Ser Gly Ser Ser Ile Thr
        115                 120                 125

Thr Leu Ser Ser Gly Pro His Ser Leu Ser Pro Ala Ser Asp Ile Leu
    130                 135                 140

Thr Thr Leu Ser Ser Thr Thr Glu Thr Ala Ala Pro Ala Val Ala Asp
145                 150                 155                 160

Ala Arg Lys Pro Pro Ser Gly Lys Lys Lys
                165                 170

<210> SEQ ID NO 3
<211> LENGTH: 257
<212> TYPE: PRT
<213> ORGANISM: human herpesvirus 8

<400> SEQUENCE: 3

Met Ala Thr Ala Asn Asn Pro Pro Ser Gly Leu Leu Asp Pro Thr Leu
1               5                   10                  15

Cys Glu Asp Arg Ile Phe Tyr Asn Ile Leu Glu Ile Glu Pro Arg Phe
                20                  25                  30

Leu Thr Ser Asp Ser Val Phe Gly Thr Phe Gln Gln Ser Leu Thr Ser
            35                  40                  45

His Met Arg Lys Leu Leu Gly Thr Trp Met Phe Ser Val Cys Gln Glu
        50                  55                  60

Tyr Asn Leu Glu Pro Asn Val Val Ala Leu Ala Leu Asn Leu Leu Asp
```

```
                65                  70                  75                  80
Arg Leu Leu Leu Ile Lys Gln Val Ser Lys Glu His Phe Gln Lys Thr
                    85                  90                  95

Gly Ser Ala Cys Leu Leu Val Ala Ser Lys Leu Arg Ser Leu Thr Pro
                    100                 105                 110

Ile Ser Thr Ser Ser Leu Cys Tyr Ala Ala Ala Asp Ser Phe Ser Arg
                    115                 120                 125

Gln Glu Leu Ile Asp Gln Glu Lys Glu Leu Leu Glu Lys Leu Ala Trp
            130                 135                 140

Arg Thr Glu Ala Val Leu Ala Thr Asp Val Thr Ser Phe Leu Leu Leu
145                 150                 155                 160

Lys Leu Leu Gly Gly Ser Gln His Leu Asp Phe Trp His His Glu Val
                    165                 170                 175

Asn Thr Leu Ile Thr Lys Ala Leu Val Asp Pro Lys Thr Gly Ser Leu
                    180                 185                 190

Pro Ala Ser Ile Ile Ser Ala Ala Gly Cys Ala Leu Leu Val Pro Ala
                    195                 200                 205

Asn Val Ile Pro Gln Asp Thr His Ser Gly Gly Val Val Pro Gln Leu
            210                 215                 220

Ala Ser Ile Leu Gly Cys Asp Val Ser Val Leu Gln Ala Ala Val Glu
225                 230                 235                 240

Gln Ile Leu Thr Ser Val Ser Asp Phe Asp Leu Arg Ile Leu Asp Ser
                    245                 250                 255

Tyr

<210> SEQ ID NO 4
<211> LENGTH: 1129
<212> TYPE: PRT
<213> ORGANISM: human herpesvirus 8

<400> SEQUENCE: 4

Met Ala Pro Pro Gly Met Arg Leu Arg Ser Gly Arg Ser Thr Gly Ala
1               5                   10                  15

Pro Leu Thr Arg Gly Ser Cys Arg Lys Arg Asn Arg Ser Pro Glu Arg
                20                  25                  30

Cys Asp Leu Gly Asp Asp Leu His Leu Gln Pro Arg Arg Lys His Val
            35                  40                  45

Ala Asp Ser Val Asp Gly Arg Glu Cys Gly Pro His Thr Leu Pro Ile
50                  55                  60

Pro Gly Ser Pro Thr Val Phe Thr Ser Gly Leu Pro Ala Phe Val Ser
65                  70                  75                  80

Ser Pro Thr Leu Pro Val Ala Pro Ile Pro Ser Pro Ala Pro Ala Thr
                85                  90                  95

Pro Leu Pro Pro Pro Ala Leu Leu Pro Pro Val Thr Thr Ser Ser Ser
                    100                 105                 110

Pro Ile Pro Pro Ser His Pro Val Ser Pro Gly Thr Thr Asp Thr His
            115                 120                 125

Ser Pro Ser Pro Ala Leu Pro Pro Thr Gln Ser Pro Glu Ser Ser Gln
            130                 135                 140

Arg Pro Pro Leu Ser Ser Pro Thr Gly Arg Pro Asp Ser Ser Thr Pro
145                 150                 155                 160

Met Arg Pro Pro Pro Ser Gln Gln Thr Thr Pro Pro His Ser Pro Thr
                    165                 170                 175

Thr Pro Pro Pro Glu Pro Pro Ser Lys Ser Ser Pro Asp Ser Leu Ala
```

```
                    180                 185                 190
Pro Ser Thr Leu Arg Ser Leu Arg Lys Arg Leu Ser Ser Pro Gln
            195                 200                 205
Gly Pro Ser Thr Leu Asn Pro Ile Cys Gln Ser Pro Val Ser Pro
        210                 215                 220
Pro Arg Cys Asp Phe Ala Asn Arg Ser Val Tyr Pro Pro Trp Ala Thr
225                 230                 235                 240
Glu Ser Pro Ile Tyr Val Gly Ser Ser Asp Gly Asp Thr Pro Pro
                245                 250                 255
Arg Gln Pro Pro Thr Ser Pro Ile Ser Ile Gly Ser Ser Ser Pro Ser
            260                 265                 270
Glu Gly Ser Trp Gly Asp Asp Thr Ala Met Leu Val Leu Leu Ala Glu
        275                 280                 285
Ile Ala Glu Glu Ala Ser Lys Asn Glu Lys Glu Cys Ser Glu Asn Asn
290                 295                 300
Gln Ala Gly Glu Asp Asn Gly Asp Asn Glu Ile Ser Lys Glu Ser Gln
305                 310                 315                 320
Val Asp Lys Asp Asp Asn Asp Asn Lys Asp Asp Glu Glu Gln Glu
                325                 330                 335
Thr Asp Glu Glu Asp Glu Asp Glu Glu Asp Asp Glu Glu Asp
            340                 345                 350
Asp Glu Glu Asp Glu Glu Asp Glu Glu Asp Glu Glu Asp
        355                 360                 365
Asp Glu Glu Asp Glu Glu Asp Glu Glu Asp Glu Glu
        370                 375                 380
Asp Glu Glu Glu Glu Glu Asp Glu Glu Asp Asp Asp Glu Asp Asn
385                 390                 395                 400
Glu Asp Glu Glu Asp Asp Glu Glu Asp Lys Lys Glu Asp Glu Glu
                405                 410                 415
Asp Gly Gly Asp Gly Asn Lys Thr Leu Ser Ile Gln Ser Ser Gln Gln
            420                 425                 430
Gln Gln Glu Pro Gln Gln Gln Glu Pro Gln Gln Gln Glu Pro Gln Gln
        435                 440                 445
Gln Glu Pro Gln Gln Gln Pro Gln Gln Gln Pro Gln Gln Gln
        450                 455                 460
Glu Pro Gln Gln Glu Pro Gln Gln Arg Glu Pro Gln Gln Arg Glu
465                 470                 475                 480
Pro Gln Gln Arg Glu Pro Gln Gln Arg Glu Pro Gln Gln Arg Glu Pro
                485                 490                 495
Gln Gln Arg Glu Pro Gln Gln Arg Glu Pro Gln Gln Arg Glu Pro Gln
            500                 505                 510
Gln Arg Glu Pro Gln Gln Arg Glu Pro Gln Gln Arg Glu Pro Gln Gln
        515                 520                 525
Arg Glu Pro Gln Gln Glu Pro Gln Gln Glu Pro Gln Gln
530                 535                 540
Glu Pro Gln Gln Gln Glu Pro Gln Gln Glu Pro Gln Gln Glu
545                 550                 555                 560
Pro Gln Gln Gln Glu Pro Gln Gln Glu Pro Gln Gln Glu Pro
                565                 570                 575
Gln Gln Gln Glu Pro Gln Gln Glu Pro Gln Gln Glu Pro Gln
            580                 585                 590
Gln Gln Asp Glu Gln Gln Asp Glu Gln Gln Asp Glu Gln Gln
        595                 600                 605
```

-continued

Gln Asp Glu Gln Gln Gln Asp Glu Gln Gln Asp Glu Gln Gln Gln
    610                 615                 620
Asp Glu Gln Gln Gln Asp Glu Gln Gln Gln Asp Glu Gln Gln Gln
625                 630                 635                 640
Asp Glu Gln Gln Gln Asp Glu Gln Gln Gln Glu Gln Glu Gln Glu
        645                 650                 655
Gln Gln Glu Gln Gln Gln Gln Asp Glu Gln Gln Asp Glu Gln Gln
            660                 665                 670
Gln Asp Glu Gln Gln Gln Asp Glu Gln Gln Gln Asp Glu Gln Gln
        675                 680                 685
Gln Asp Glu Gln Gln Gln Gln Asp Glu Gln Gln Gln Glu Gln Glu
    690                 695                 700
Glu Gln Gln Glu Glu Gln Gln Gln Glu Gln Gln Glu Gln Gln Glu
705                 710                 715                 720
Glu Gln Glu Gln Glu Leu Glu Glu Gln Glu Gln Glu Leu Glu Gln
                725                 730                 735
Glu Gln Glu Leu Glu Glu Gln Glu Gln Glu Leu Glu Glu Gln Gln
            740                 745                 750
Glu Leu Glu Glu Gln Glu Glu Leu Glu Glu Gln Glu Glu Glu Leu
        755                 760                 765
Glu Glu Gln Glu Gln Glu Leu Glu Glu Gln Glu Gln Glu Leu Glu
    770                 775                 780
Gln Glu Gln Glu Leu Glu Glu Gln Glu Gln Glu Leu Glu Glu Glu
785                 790                 795                 800
Gln Glu Leu Glu Gln Glu Gln Glu Leu Glu Glu Gln Glu Glu Glu
                805                 810                 815
Leu Glu Glu Gln Glu Gln Glu Gln Glu Leu Glu Glu Val Glu Glu Gln
            820                 825                 830
Glu Gln Glu Gln Glu Gln Glu Leu Glu Glu Val Glu Glu Gln Glu
        835                 840                 845
Gln Glu Gln Glu Gln Glu Gln Glu Leu Glu Glu Val Glu Glu Glu
    850                 855                 860
Gln Glu Glu Gln Glu Leu Glu Glu Val Glu Glu Gln Glu Glu Gln Glu
865                 870                 875                 880
Leu Glu Glu Val Glu Glu Gln Glu Gln Gln Gly Val Glu Gln Gln Glu
                885                 890                 895
Gln Glu Thr Val Glu Glu Pro Ile Ile Leu His Gly Ser Ser Glu
            900                 905                 910
Asp Glu Met Glu Val Asp Tyr Pro Val Val Ser Thr His Glu Gln Ile
        915                 920                 925
Ala Ser Ser Pro Pro Gly Asp Asn Thr Pro Asp Asp Pro Gln Pro
    930                 935                 940
Gly Pro Ser Arg Glu Tyr Arg Tyr Val Leu Arg Thr Ser Pro His
945                 950                 955                 960
Arg Pro Gly Val Arg Met Arg Arg Val Pro Val Thr His Pro Lys Lys
                965                 970                 975
Pro His Pro Arg Tyr Gln Gln Pro Pro Val Pro Tyr Arg Gln Ile Asp
            980                 985                 990
Asp Cys Pro Ala Lys Ala Arg Pro  Gln His Ile Phe Tyr Arg Arg Phe
        995                 1000                1005
Leu Gly Lys Asp Gly Arg Arg Asp Pro Lys Cys Gln Trp Lys Phe
    1010                1015                1020

```
Ala Val Ile Phe Trp Gly Asn Asp Pro Tyr Gly Leu Lys Lys Leu
    1025                1030                1035

Ser Gln Ala Phe Gln Phe Gly Val Lys Ala Gly Pro Val Ser
    1040                1045                1050

Cys Leu Pro His Pro Gly Asp Gln Ser Pro Ile Thr Tyr Cys
    1055                1060                1065

Val Tyr Val Tyr Cys Gln Asn Lys Asp Thr Ser Lys Lys Val Gln
    1070                1075                1080

Met Ala Arg Leu Ala Trp Glu Ala Ser His Pro Leu Ala Gly Asn
    1085                1090                1095

Leu Gln Ser Ser Ile Val Lys Phe Lys Lys Pro Leu Pro Leu Thr
    1100                1105                1110

Gln Pro Gly Glu Asn Gln Gly Pro Gly Asp Ser Pro Gln Glu Met
    1115                1120                1125

Thr

<210> SEQ ID NO 5
<211> LENGTH: 204
<212> TYPE: PRT
<213> ORGANISM: human herpesvirus

<400> SEQUENCE: 5

His Ala Asn Cys Pro Thr Tyr Arg Ser His Leu Gly Phe Trp Gln Glu
1               5                   10                  15

Gly Trp Ser Gly Gln Val Tyr Gln Asp Trp Leu Gly Arg Met Asn Cys
            20                  25                  30

Ser Tyr Glu Asn Met Thr Ala Leu Glu Ala Val Ser Leu Asn Gly Thr
        35                  40                  45

Arg Leu Ala Ala Gly Ser Pro Ser Ser Glu Tyr Pro Asn Val Ser Val
    50                  55                  60

Ser Val Glu Asp Thr Ser Ala Ser Gly Ser Gly Glu Asp Ala Ile Asp
65                  70                  75                  80

Glu Ser Gly Ser Gly Glu Glu Arg Pro Val Thr Ser His Val Thr
                85                  90                  95

Phe Met Thr Gln Ser Val Gln Ala Thr Thr Glu Leu Thr Asp Ala Leu
            100                 105                 110

Ile Ser Ala Phe Ser Gly Ser Tyr Ser Ser Gly Glu Pro Ser Arg Thr
        115                 120                 125

Thr Arg Ile Arg Val Ser Pro Val Ala Glu Asn Gly Arg Asn Ser Gly
    130                 135                 140

Ala Ser Asn Arg Val Pro Phe Ser Ala Thr Thr Thr Thr Arg Gly
145                 150                 155                 160

Arg Asp Ala His Tyr Asn Ala Glu Ile Arg Thr His Leu Tyr Ile Leu
                165                 170                 175

Trp Ala Val Gly Leu Leu Leu Gly Leu Val Leu Ile Leu Tyr Leu Cys
            180                 185                 190

Val Pro Arg Cys Arg Arg Lys Lys Pro Tyr Ile Val
            195                 200

<210> SEQ ID NO 6
<211> LENGTH: 169
<212> TYPE: PRT
<213> ORGANISM: human herpesvirus 8

<400> SEQUENCE: 6

Ser Asn Phe Lys Val Arg Asp Pro Val Ile Gln Glu Arg Leu Asp His
```

```
                1               5              10              15

Asp Tyr Ala His His Pro Leu Val Ala Arg Met Asn Thr Leu Asp Gln
                            20              25              30

Gly Asn Met Ser Gln Ala Glu Tyr Leu Val Gln Lys Arg His Tyr Leu
                        35              40              45

Val Phe Leu Ile Ala His His Tyr Tyr Glu Ala Tyr Leu Arg Arg Met
                    50              55              60

Gly Gly Ile Gln Arg Arg Asp His Leu Gln Thr Leu Arg Asp Gln Lys
          65                  70              75                  80

Pro Arg Glu Arg Ala Asp Arg Val Ser Ala Ser Ala Tyr Asp Ala
                            85              90              95

Gly Thr Phe Thr Val Pro Ser Arg Pro Gly Pro Ala Ser Gly Thr Thr
                            100             105             110

Pro Gly Gly Gln Asp Ser Leu Gly Val Ser Gly Ser Ile Thr Thr
                        115             120             125

Leu Ser Ser Gly Pro His Ser Leu Ser Pro Ala Ser Asp Ile Leu Thr
                    130             135             140

Thr Leu Ser Ser Thr Thr Glu Thr Ala Ala Pro Ala Val Ala Asp Ala
          145                 150             155                 160

Arg Lys Pro Pro Ser Gly Lys Lys Lys
                            165

<210> SEQ ID NO 7
<211> LENGTH: 256
<212> TYPE: PRT
<213> ORGANISM: human herpesvirus 8

<400> SEQUENCE: 7

Ala Thr Ala Asn Asn Pro Pro Ser Gly Leu Leu Asp Pro Thr Leu Cys
          1               5              10              15

Glu Asp Arg Ile Phe Tyr Asn Ile Leu Glu Ile Glu Pro Arg Phe Leu
                            20              25              30

Thr Ser Asp Ser Val Phe Gly Thr Phe Gln Gln Ser Leu Thr Ser His
                        35              40              45

Met Arg Lys Leu Leu Gly Thr Trp Met Phe Ser Val Cys Gln Glu Tyr
                    50              55              60

Asn Leu Glu Pro Asn Val Val Ala Leu Ala Leu Asn Leu Leu Asp Arg
          65                  70              75                  80

Leu Leu Leu Ile Lys Gln Val Ser Lys Glu His Phe Gln Lys Thr Gly
                            85              90              95

Ser Ala Cys Leu Leu Val Ala Ser Lys Leu Arg Ser Leu Thr Pro Ile
                            100             105             110

Ser Thr Ser Ser Leu Cys Tyr Ala Ala Ala Asp Ser Phe Ser Arg Gln
                        115             120             125

Glu Leu Ile Asp Gln Glu Lys Glu Leu Leu Lys Leu Ala Trp Arg
                    130             135             140

Thr Glu Ala Val Leu Ala Thr Asp Val Thr Ser Phe Leu Leu Leu Lys
          145                 150             155                 160

Leu Leu Gly Gly Ser Gln His Leu Asp Phe Trp His His Glu Val Asn
                            165             170             175

Thr Leu Ile Thr Lys Ala Leu Val Asp Pro Lys Thr Gly Ser Leu Pro
                            180             185             190

Ala Ser Ile Ile Ser Ala Ala Gly Cys Ala Leu Leu Val Pro Ala Asn
                        195             200             205
```

```
Val Ile Pro Gln Asp Thr His Ser Gly Gly Val Pro Gln Leu Ala
210                 215                 220

Ser Ile Leu Gly Cys Asp Val Ser Val Leu Gln Ala Ala Val Glu Gln
225                 230                 235                 240

Ile Leu Thr Ser Val Ser Asp Phe Asp Leu Arg Ile Leu Asp Ser Tyr
                245                 250                 255
```

<210> SEQ ID NO 8
<211> LENGTH: 652
<212> TYPE: PRT
<213> ORGANISM: human herpesvirus 8

<400> SEQUENCE: 8

```
Gly Ser Trp Gly Asp Asp Thr Ala Met Leu Val Leu Leu Ala Glu Ile
1               5                   10                  15

Ala Glu Glu Ala Ser Lys Asn Glu Lys Glu Cys Ser Glu Asn Asn Gln
                20                  25                  30

Ala Gly Glu Asp Asn Gly Asp Asn Glu Ile Ser Lys Glu Ser Gln Val
            35                  40                  45

Asp Lys Asp Asp Asn Asp Asn Lys Asp Asp Glu Glu Gln Glu Thr
        50                  55                  60

Asp Glu Glu Asp Glu Glu Asp Asp Glu Asp Glu Glu Asp Asp
65                  70                  75                  80

Glu Glu Asp Asp Glu Asp Asp Glu Glu Asp Asp Glu Glu Asp Asp
                85                  90                  95

Glu Glu Glu Asp Glu Glu Glu Asp Glu Glu Asp Glu Glu Glu Asp
            100                 105                 110

Glu Glu Glu Glu Glu Asp Glu Glu Asp Asp Asp Asp Glu Asp Asn Glu
        115                 120                 125

Asp Glu Glu Asp Asp Glu Glu Glu Asp Lys Lys Glu Asp Glu Glu Asp
130                 135                 140

Gly Gly Asp Gly Asn Lys Thr Leu Ser Ile Gln Ser Ser Gln Gln
145                 150                 155                 160

Gln Glu Pro Gln Gln Gln Glu Pro Gln Gln Glu Pro Gln Gln
                165                 170                 175

Glu Pro Gln Gln Glu Pro Gln Gln Glu Pro Gln Gln Glu
            180                 185                 190

Pro Gln Gln Gln Glu Pro Gln Gln Arg Glu Pro Gln Gln Arg Glu Pro
        195                 200                 205

Gln Gln Arg Glu Pro Gln Gln Arg Glu Pro Gln Gln Arg Glu Pro Gln
210                 215                 220

Gln Arg Glu Pro Gln Gln Arg Glu Pro Gln Gln Arg Glu Pro Gln
225                 230                 235                 240

Arg Glu Pro Gln Gln Arg Glu Pro Gln Gln Arg Glu Pro Gln Gln Arg
                245                 250                 255

Glu Pro Gln Gln Gln Glu Pro Gln Gln Gln Glu Pro Gln Gln Gln Glu
            260                 265                 270

Pro Gln Gln Gln Glu Pro Gln Gln Gln Glu Pro Gln Gln Gln Glu Pro
        275                 280                 285

Gln Gln Gln Glu Pro Gln Gln Glu Pro Gln Gln Glu Pro Gln
290                 295                 300

Gln Gln Glu Pro Gln Gln Gln Glu Pro Gln Gln Gln Glu Pro Gln Gln
305                 310                 315                 320

Gln Asp Glu Gln Gln Asp Glu Gln Gln Asp Glu Gln Gln
                325                 330                 335
```

Asp Glu Gln Gln Gln Asp Glu Gln Gln Gln Asp Gln Gln Asp
                340                 345                 350

Glu Gln Gln Gln Asp Glu Gln Gln Gln Asp Glu Gln Gln Asp
            355                 360                 365

Glu Gln Gln Gln Asp Glu Gln Gln Gln Glu Glu Gln Glu Gln
    370                 375                 380

Gln Glu Glu Gln Gln Asp Glu Gln Gln Asp Glu Gln Gln Gln
385                 390                 395                 400

Asp Glu Gln Gln Gln Asp Glu Gln Gln Gln Asp Glu Gln Gln
                405                 410                 415

Asp Glu Gln Gln Gln Asp Glu Gln Gln Gln Glu Glu Gln Glu
        420                 425                 430

Gln Gln Glu Gln Gln Glu Gln Glu Gln Glu Gln Gln Glu Glu
    435                 440                 445

Gln Glu Gln Gln Leu Glu Gln Gln Gln Glu Leu Glu Gln Glu
    450                 455                 460

Gln Glu Leu Glu Gln Gln Gln Gln Leu Glu Gln Gln Gln Glu
465                 470                 475                 480

Leu Glu Glu Gln Glu Gln Glu Leu Glu Glu Gln Glu Leu Glu
                485                 490                 495

Glu Gln Glu Gln Glu Leu Glu Gln Glu Glu Glu Leu Glu Gln
        500                 505                 510

Glu Gln Glu Leu Glu Glu Gln Gln Glu Leu Glu Glu Glu Gln
    515                 520                 525

Glu Leu Glu Gln Glu Gln Glu Leu Glu Gln Glu Gln Glu Leu
    530                 535                 540

Glu Glu Gln Glu Gln Glu Gln Glu Leu Glu Glu Val Glu Glu Gln
545                 550                 555                 560

Gln Glu Gln Glu Gln Glu Gln Glu Leu Glu Glu Val Glu Glu Gln
            565                 570                 575

Glu Glu Glu Glu Gln Glu Glu Gln Leu Glu Glu Val Glu Glu Gln
        580                 585                 590

Glu Glu Gln Glu Leu Glu Glu Val Glu Glu Gln Glu Glu Gln Leu
    595                 600                 605

Glu Glu Val Glu Glu Gln Glu Gln Gln Gly Val Glu Gln Gln Glu Gln
610                 615                 620

Glu Thr Val Glu Glu Pro Ile Ile Leu His Gly Ser Ser Glu Asp
625                 630                 635                 640

Glu Met Glu Val Asp Tyr Pro Val Val Ser Thr His
                645                 650

<210> SEQ ID NO 9
<211> LENGTH: 687
<212> TYPE: DNA
<213> ORGANISM: human herpesvirus 8

<400> SEQUENCE: 9
atgagttcca cacagattcg cacagaaatc cctgtggcgc tcctaatcct atgcctttgt    60
ctggtggcgt gccatgccaa ttgtcccacg tatcgttcgc atttgggatt ctggcaagag   120
ggttggagtg acaggtttta tcaggactgg ctaggcagga tgaactgttc ctacgagaat   180
atgacggccc tagaggccgt ctccctaaac gggaccagac tagcagctgg atctccgtcg   240
agtgagtatc caaatgtctc cgtatctgtt gaagatacgt ctgcctctgg gtctggagaa   300

```
gatgcaatag atgaatcggg gtcgggggag gaagagcgtc ccgtgacctc ccacgtgact    360
tttatgacac aaagcgtcca ggccaccaca gaactgaccg atgccttaat atcagccttt    420
tcaggatcat attcatctgg ggaaccatcc aggaccacgc gaattcgcgt atcaccggtc    480
gcagaaaacg gcagaaatag tggtgctagt aaccgtgtgc cattttctgc caccactaca    540
acgactagag gaagagacgc gcactacaat gcagaaatac ggacccatct ttacatacta    600
tgggctgtgg gttattgct gggacttgtc cttatacttt acctgtgcgt tccacgatgc    660
cggcgtaaga aaccctacat agtgtaa                                         687

<210> SEQ ID NO 10
<211> LENGTH: 513
<212> TYPE: DNA
<213> ORGANISM: human herpesvirus 8

<400> SEQUENCE: 10
ctatttcttt ttgccagagg ggggtttcct cgcgtcggcc accgcggggg cggccgtttc     60
cgtcgtggat gagagggttg tgagaatgtc tgacgccggc gacaatgaat ggggaccaga    120
ggacagggtg ttatactgc ttcccgagac ccccagtgag tcctggcccc cgggcgtggt    180
gccggatgca gggcctggcc tcgaaggcac ggtgaacgtc cccgcgtcgt aagccgacgc    240
cgcggaaact cggtcagcgc gctcgcgcgg tttctgatcc ctaagggtct gcagatgatc    300
ccgcctttga attccaccca tcctcctcag ataggcctca taataatgat gggcaattaa    360
gaacacgaga tagtgtctct tttgcacgag gtattcggcc tgcgacatat ttccctgatc    420
cagggtattc atgcgagcca ccaggggatg gtgagcgtag tcatgatcca gtcgctcctg    480
gatcacgggg tctctcacct taaagttgga cat                                 513

<210> SEQ ID NO 11
<211> LENGTH: 774
<212> TYPE: DNA
<213> ORGANISM: human herpesvirus 8

<400> SEQUENCE: 11
ttaatagctg tccagaatgc gcagatcaaa gtccgaaaca gatgttagga tctgttccac     60
tgccgcctgt agaacggaaa catcgcatcc aatatgctt gccagctgag gaactacccc    120
acccgagtgg gtatcctgcg gaatgacgtt ggcaggaacc aacagcgcac agcctgcagc    180
gctgataata gaggcgggca atgagccagt ctttgggtca actaaggctt ttgtaatcag    240
ggtgttgacc tcgtggtgcc aaaagtccag gtgttgggag ccccccagca atttaagtaa    300
caagaaggaa gtgacgtccg tcgctaagac tgcctctgtt cgccacgcca acttctcaag    360
gagttctttc tcctggtcta taagttcttg gcgggaaaag gagtctgccg cggcatagca    420
aagtgaactg gtagaaatag gcgtgaggct tctgagctta ctggccacta acaggcaggc    480
gctccctgtc ttttgaaagt gttctttgga cacctgcttt ataagtagga gtctgtccaa    540
aagattaagg gccaacgcga ccacgttagg ttctaggttg tattcctggc aaactgaaaa    600
catccatgtg cccagtaact tacgcatatg cgaagtaaga gattgttgaa aggtcccaaa    660
tacagagtca gaagttaaaa agcgcggctc aatttcaaga atattgtaaa agatccgatc    720
ctcacatagc gtgggatcca gaagtcccga gggcgggtta ttggcagttg ccat           774

<210> SEQ ID NO 12
<211> LENGTH: 3390
<212> TYPE: DNA
<213> ORGANISM: human herpesvirus 8
```

<400> SEQUENCE: 12

```
ttatgtcatt tcctgtggag agtccccagg accttggttt tcccctggct gggttaatgg        60
caggggcttt ttaaacttaa ctatggaaga ttgtaggttt cctgccaggg ggtgactagc       120
ttcccaggct aggcgggcca tttgtacttt cttacttgtg tctttgttct gacaatacac       180
atatacacaa taagttatgg gcgactggtc tggtccaggg tggggcaagc aggacacggg       240
gcctgccttt actcctccaa actggaaggc ctgagataat tttttaagtc cgtatgggtc       300
attgccccaa aaaatcactg caaacttcca ttgacacttt ggatctcgtc ttccatcctt       360
tcccaaaaag cgtctataaa agatgtgttg tggcctagct ttcgcaggac aatcatctat       420
ctgtctgtaa gggaccggtg gttgttggta tcttggatgt ggcttttttg ggtgggtaac       480
tggaacgcgc tcatacgaa ctccaggtct gtggggtggt gatgttctga gtacatagcg        540
gtattcgcga gatgggccag gttgtgggtc atcgtctggt gtattatctc ctggtgggct       600
actggcaatt tgttcatgtg tgctaacaac agggtaatcc acttccattt cgtcctcgga       660
tgacgacccg tgcaagatta tgggctcttc caccgtctcc tgctcctgct gttccacccc       720
ctgctgctcc tgctcttcca cctcctctaa ctcctgctct tcctgctctt ccacctcctc       780
taactcctgc tcttcctgct cttccacctc tctaactcc tgctcctcct gctcctcctg        840
ctcctgctct tgctcctcca cctcctctaa ttcctgctct tcctgctcct gctcttgctc       900
ttccacctcc tctaactcct gctcctgctc ctgctcctct aactcctgct cctgctcctc       960
taactcctgc tcctgctcct ctaactcctg ctcctgctcc tctaactcct gctcctgctc      1020
ctctaactcc tgctcctgct cctctaactc tgctcctgc tcctctaact cctgctcctg       1080
ctcctctaac tcctgctcct gctcctctaa ctcctgctcc tgctcctcta actcctgctc      1140
ctgctcctct aactcctgct cctgctcctc taactcctgc tcctgctcct ctaactcctg      1200
ctcctgctcc tctaactcct gctcctgctc ctgctcctgc tcctgctcct cctgctgctc      1260
ctgctcctcc tgctgctcct gctcctcctg ctgctcctgt tcatcctgct gctgctgctc      1320
atcctgctgc tgctcatcct gctgctcctg ctcatcctgc tgctgctcat cctgctgctg      1380
ctcatcctgc tgctgctcat cctgctgctg ctcctcctgc tgctcctgct cctcctgctg      1440
ctcctgttca tcctgctgct gctgctcatc ctgctgctgc tcatcctgct gctcctgctc      1500
atcctgctgc tgctcatcct gctgctgctc atcctgctgc tgctcatcct gctgctgctc      1560
atcctgctgc tgctcatcct gctgctgctc atcctgctgc tgctcatcct gctgctgtgg      1620
ctcctgctgt tgtggctcct gctgttgtgg ctcctgctgt tgtggctcct gctgttgtgg      1680
ctcctgctgt tgtggctcct gctgctgtgg ctcctgctgc tgtggctcct gctgctgtgg      1740
ctcctgctgc tgtggctcct gctgctgtgg ctcctgctgc tgtggctcct gctgctgtgg      1800
ctcccgctgc tggggctccc gctgctgtgg ctcccgctgc tgtggctccc gctgctgtgg      1860
ctcccgctgc tggggctccc gctgctgggg ctcccgctgc tggggctccc gctgctgggg      1920
ctcccgctgc tggggctccc gctgctgtgg ctcccgctgc tgtggctccc gctgttgtgg      1980
ctcctgctgc tgtggctcct gctgttgtgg ctcctgctgc tgtggctcct gctgctgtgg      2040
ctcctgctgt tgtggctcct gctgctgtgg ctcctgctgt tgtggctcct gctgctgttg      2100
tgaactttgg atgctcaacg ttttgtttcc atcgcccccg tcctcctcgt cctccttctt      2160
gtcctcctcc tcgtcatcct cctcgtcctc attgtcctca tcgtcat cctcctcgtc         2220
ctcctcctcc tcctcgtcct cctcctcgtc ctcctcctcg tcctcctcct cgtcctcctc      2280
```

```
ctcgtcatcc tcctcgtcat cctcctcgtc atcctcctcg tcatcctcct cgtcatcctc    2340
ctcgtcatcc tcctcgtcat cctcctcgtc ctcctcatct gtctcctgct cctcctcatc    2400
atccttattg tcattgtcat ccttgtcaac ctgactttcc ttgctaatct cgttgtcccc    2460
attatcctcg ccagcctgat tattttcgga acattctttt tcattcttgg atgcttcttc    2520
tgcaatctcc gcaaggagca ccaacatggc tgtgtcatca ccccaggatc cctcagacgg    2580
ggatgatgat cctatgggaga tgggagatgt aggcggttgg cgtggcggag tatcgccatc    2640
gctggatgat cccacgtaga tcggggactc tgtggcccat ggggggtaca cactacggtt    2700
ggcgaagtca catctagggg gagagactgg gggcgactga catattgggt ttagtgtaga    2760
gggaccttgg ggggacgata gccttctttt tctcaggcta cgcagggtag acggagctaa    2820
agagtctggt gacgacttgg agggaggctc gggtggagga gtcgtgggtg agtgtggagg    2880
tgtagtctgc tgcgagggtg gcggacgcat aggtgttgaa gagtctggcc ttcctgtagg    2940
acttgaaagc ggtggccttt gagaagactc tggagactgc gtgggtggca atgcaggaga    3000
tggagaatga gtatccgtgg tccccggaga cacaggatgg gatggaggga ttggggagga    3060
agacgtggtt acgggggta agagtgccgg tggaggtaaa ggtgttgcgg gagcgggtga    3120
aggaatggga gccaccggta aagtaggact agacacaaat gctggcagcc cggatgtgaa    3180
cactgtggga cttcctggta taggcaaggt gtggggtcca cattcccggc cgtcgacgga    3240
gtcggcgaca tgcttccttc gcggttgtag atgtaggtca tcgccaaggt cacatctttc    3300
cggagacctg tttcgtttcc tacaacttcc tctcgttaag ggcgcgccgg tgctccgtcc    3360
cgacctcagg cgcattcccg ggggcgccat                                      3390
```

<210> SEQ ID NO 13
<211> LENGTH: 55
<212> TYPE: DNA
<213> ORGANISM: Artificial
<220> FEATURE:
<223> OTHER INFORMATION: Synthetic plasmid sequence

<400> SEQUENCE: 13
atcagccgcc accatggact acaaggacga cgatgacaag ggatctactt cgaaa          55

<210> SEQ ID NO 14
<211> LENGTH: 14
<212> TYPE: PRT
<213> ORGANISM: Artificial
<220> FEATURE:
<223> OTHER INFORMATION: Artificial plasmid sequence

<400> SEQUENCE: 14

Met Asp Tyr Lys Asp Asp Asp Asp Lys Gly Ser Thr Ser Lys
1               5                   10

<210> SEQ ID NO 15
<211> LENGTH: 54
<212> TYPE: DNA
<213> ORGANISM: Artificial
<220> FEATURE:
<223> OTHER INFORMATION: Artificial plasmid sequence

<400> SEQUENCE: 15
aaaaatgaac aaggatccga attcaaaaag cttctcgaga gtacttctag agcg           54

<210> SEQ ID NO 16
<211> LENGTH: 18
<212> TYPE: PRT

```
<213> ORGANISM: Artificial
<220> FEATURE:
<223> OTHER INFORMATION: Artificial plasmid sequence

<400> SEQUENCE: 16

Lys Asn Glu Gln Gly Ser Glu Phe Lys Lys Leu Leu Glu Ser Thr Ser
1               5                   10                  15

Arg Ala
```